(12) United States Patent
Griego

(10) Patent No.: US 9,044,239 B2
(45) Date of Patent: *Jun. 2, 2015

(54) MULTIPLE CLIP DEPLOYMENT MAGAZINE

(75) Inventor: John A. Griego, Blackstone, MA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 1620 days.

This patent is subject to a terminal disclaimer.

(21) Appl. No.: 12/543,928

(22) Filed: Aug. 19, 2009

(65) Prior Publication Data

US 2009/0306682 A1 Dec. 10, 2009

Related U.S. Application Data

(63) Continuation of application No. 11/032,973, filed on Jan. 11, 2005, now Pat. No. 8,080,021.

(51) Int. Cl.
| | |
|---|---|
| A61B 17/10 | (2006.01) |
| A61B 17/128 | (2006.01) |
| A61B 17/068 | (2006.01) |
| A61B 17/122 | (2006.01) |
| A61B 17/08 | (2006.01) |
| A61B 17/04 | (2006.01) |

(52) U.S. Cl.
CPC ....... *A61B 17/1285* (2013.01); *Y10T 29/53491* (2013.01); *A61B 17/068* (2013.01); *A61B 17/083* (2013.01); *A61B 17/122* (2013.01); *A61B 17/1227* (2013.01); *A61B 2017/0488* (2013.01)

(58) Field of Classification Search
USPC ............... 606/143, 157, 139, 142; 227/176.1, 227/179.1; 29/809, 811.2
See application file for complete search history.

(56) References Cited

U.S. PATENT DOCUMENTS

| | | | |
|---|---|---|---|
| 4,512,345 | A | 4/1985 | Green |
| 5,366,459 | A | 11/1994 | Yoon |

(Continued)

FOREIGN PATENT DOCUMENTS

| | | |
|---|---|---|
| AU | 2004289214 | 5/2005 |
| WO | 2005/046489 | 5/2005 |

*Primary Examiner* — Thomas McEvoy
*Assistant Examiner* — Julie A Szpira
(74) *Attorney, Agent, or Firm* — Fay Kaplun & Marcin, LLP

(57) ABSTRACT

An apparatus for deployment of multiple hemostatic clips, comprises a shaft connected to a handle and a control linkage operatively connected to the handle in combination with a magazine disposed at a distal end of the shaft, the magazine containing a plurality of clips arranged in a chain rotatable within the magazine, wherein a proximal-most one of the clips is coupled to the control linkage, a distal portion of the magazine being contoured to permit opening of a distal-most one of the clips during a distal stroke of the control linkage, and to assist closing and locking of the distal-most clip during a proximal stroke of the control linkage, the magazine including an expanded chamber sized to allow opening in any rotational orientation of a next clip located immediately proximal to the distal-most clip to a degree sufficient to disengage the distal-most clip. A method for deploying multiple hemostatic clips, comprises positioning a distal end of a magazine containing a clip chain over selected target tissue and actuating a control link of the magazine in a distal stroke to open and distally translate a distal-most clip of the clip chain in combination with orienting the open distal-most clip in a desired orientation to grasp the target tissue and actuating the control link in a proximal stroke to close and lock the distal-most clip over the target tissue. The control link is further actuated in the proximal stroke to move a next clip immediately proximal to the distal-most clip into an expanded portion of the magazine sized to allow the next clip to open to a degree sufficient to release the distal-most clip regardless of a circumferential orientation of the next clip.

13 Claims, 30 Drawing Sheets

(56) References Cited

U.S. PATENT DOCUMENTS

| | | | |
|---|---|---|---|
| 6,599,298 B1* | 7/2003 | Forster et al. | 606/139 |
| 2002/0045909 A1 | 4/2002 | Kimura et al. | |
| 2002/0151916 A1* | 10/2002 | Muramatsu et al. | 606/158 |
| 2002/0198538 A1 | 12/2002 | Kortenbach et al. | |
| 2002/0198539 A1 | 12/2002 | Sixto, Jr. et al. | |
| 2003/0069592 A1 | 4/2003 | Adams et al. | |
| 2005/0107809 A1* | 5/2005 | Litscher et al. | 606/142 |

* cited by examiner

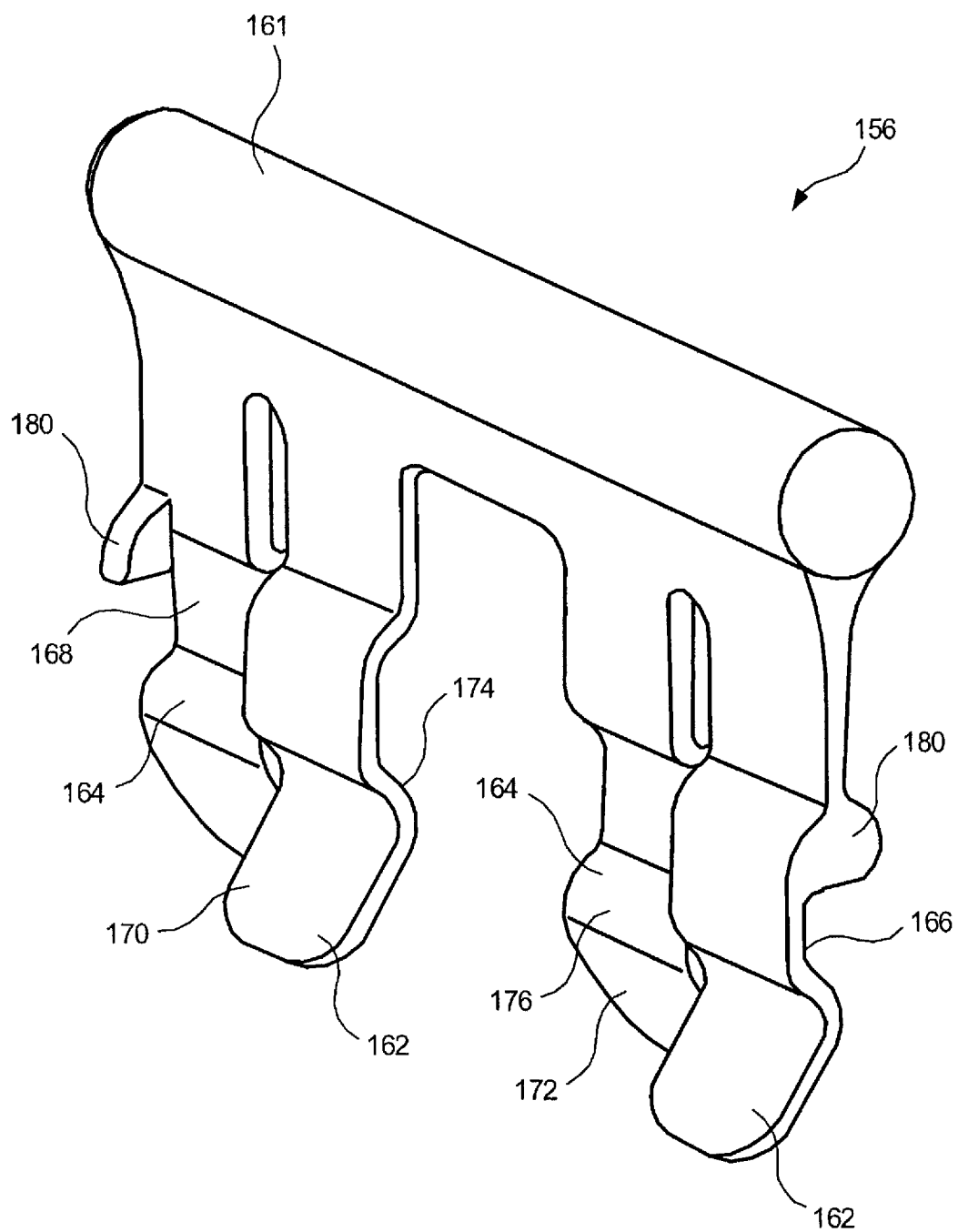
F I G. 8

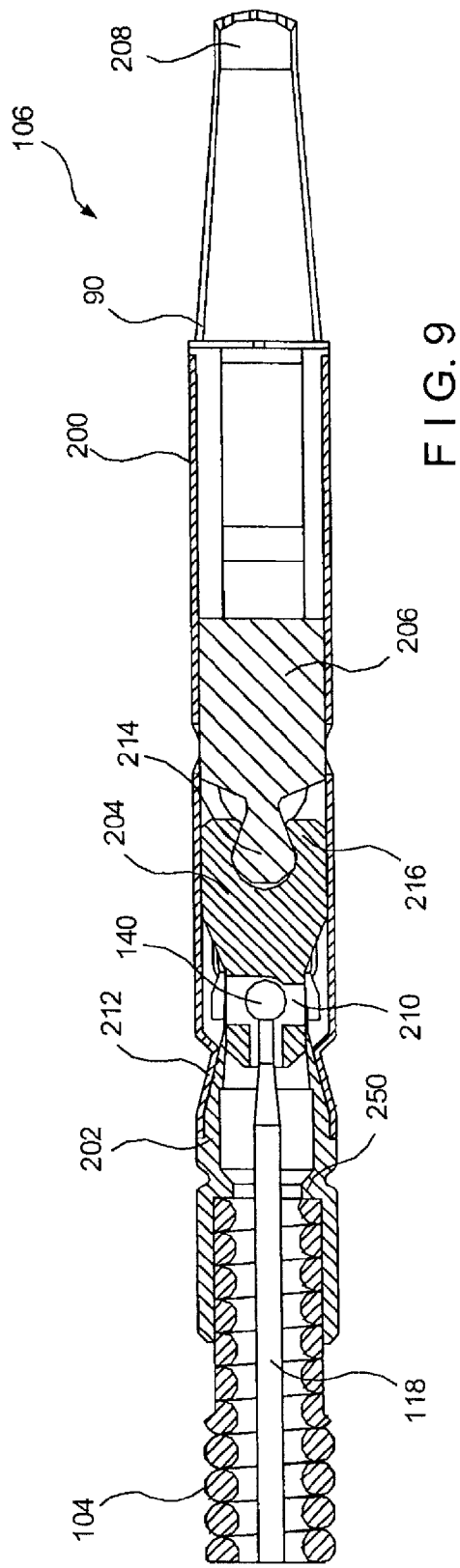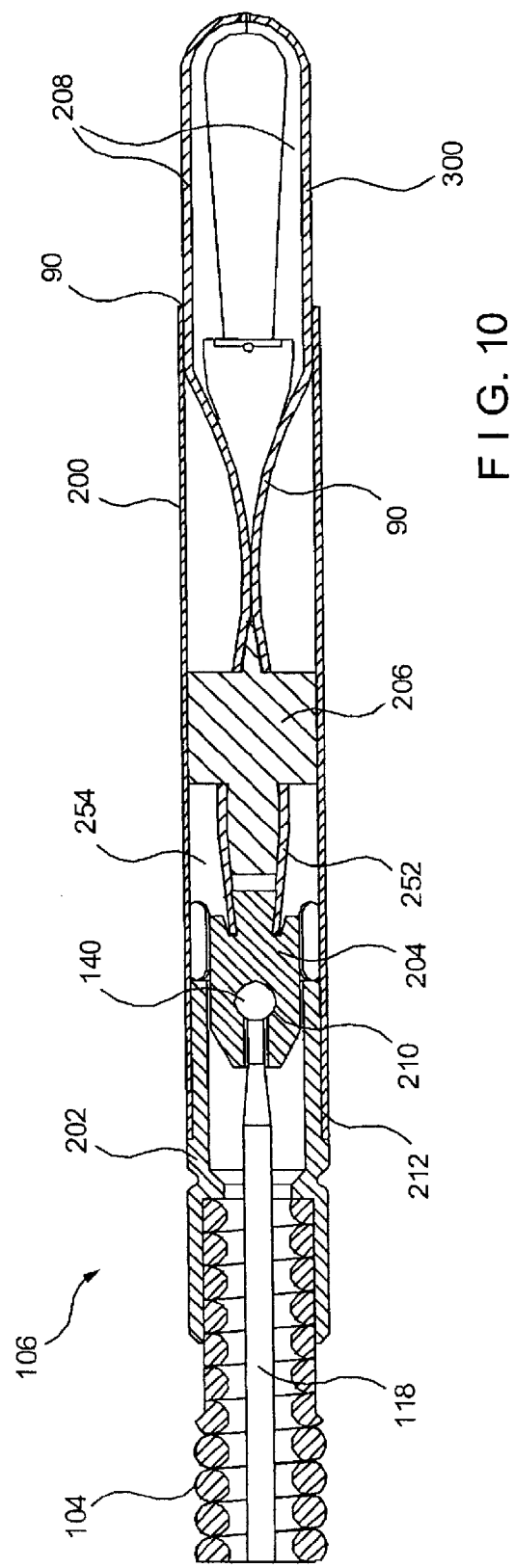

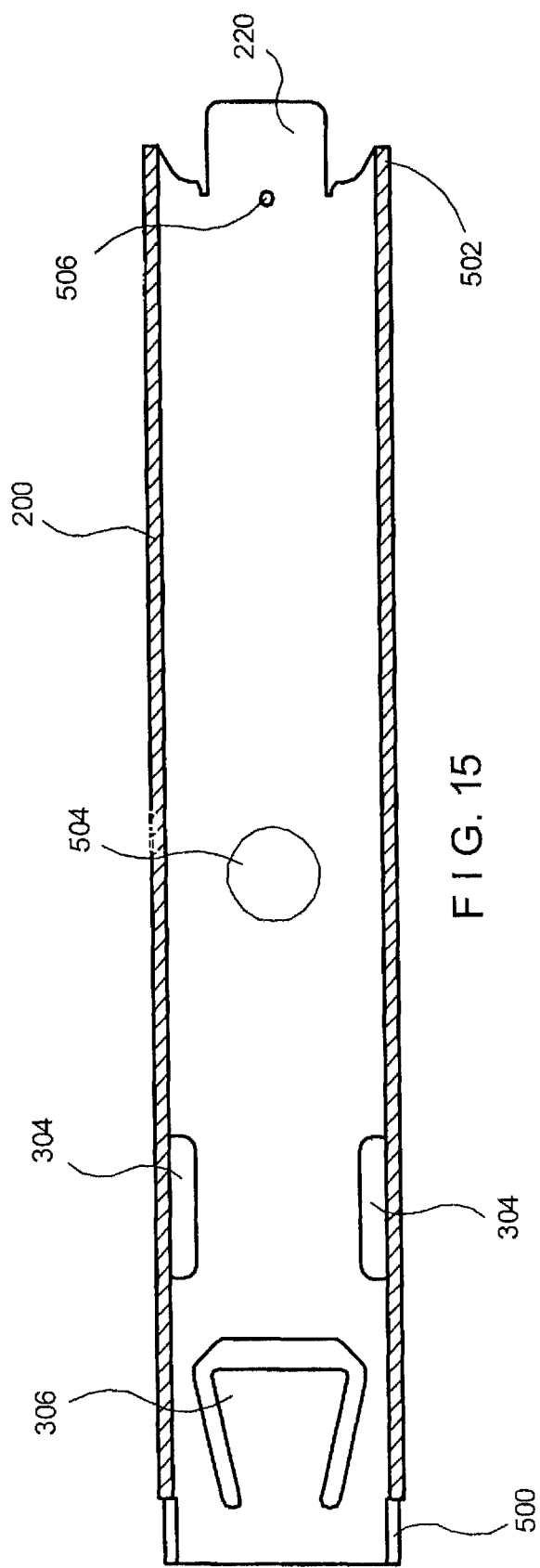

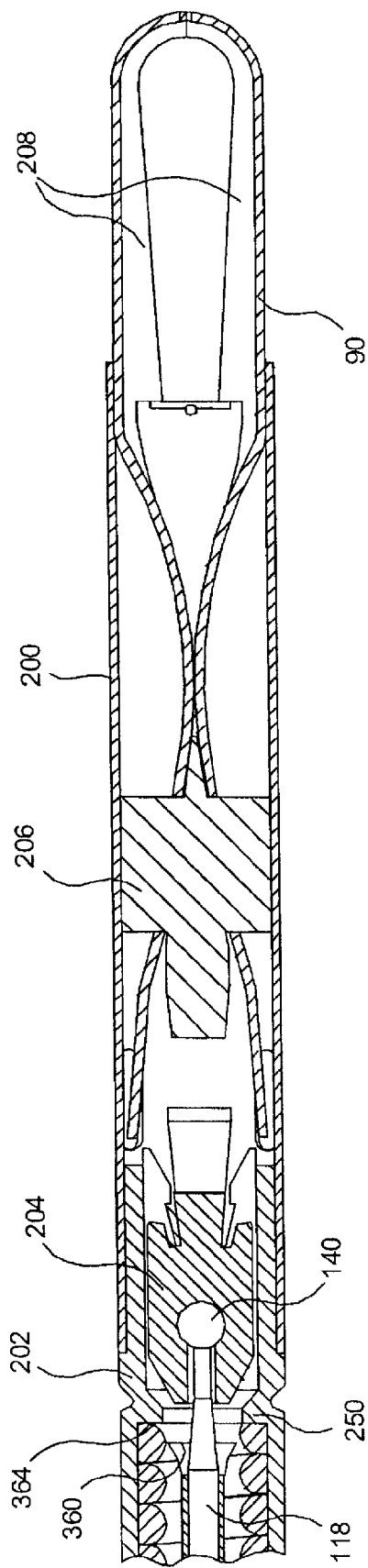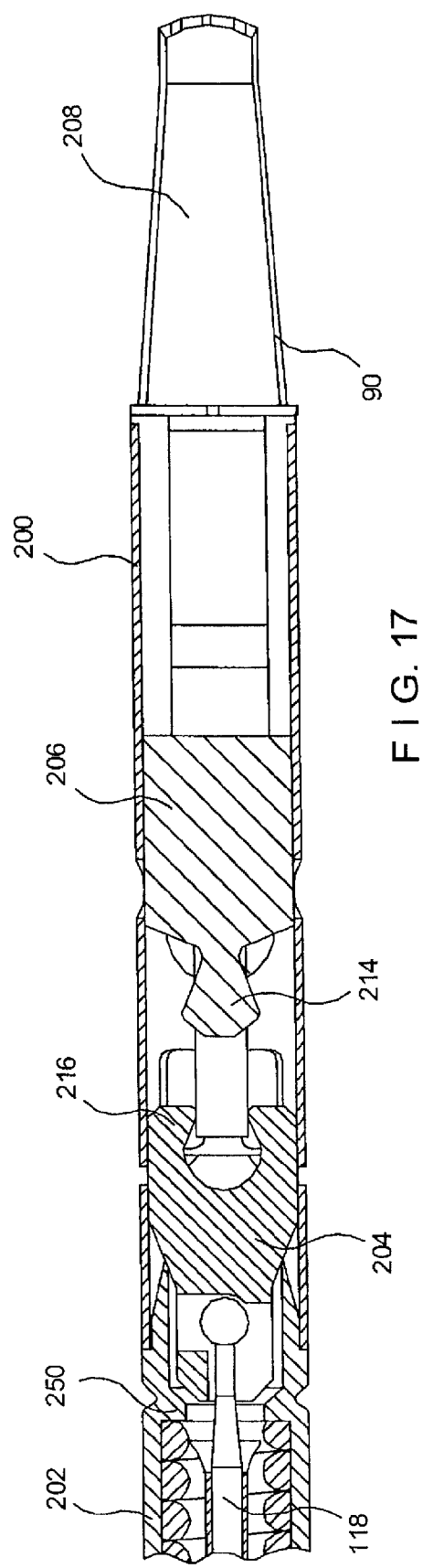

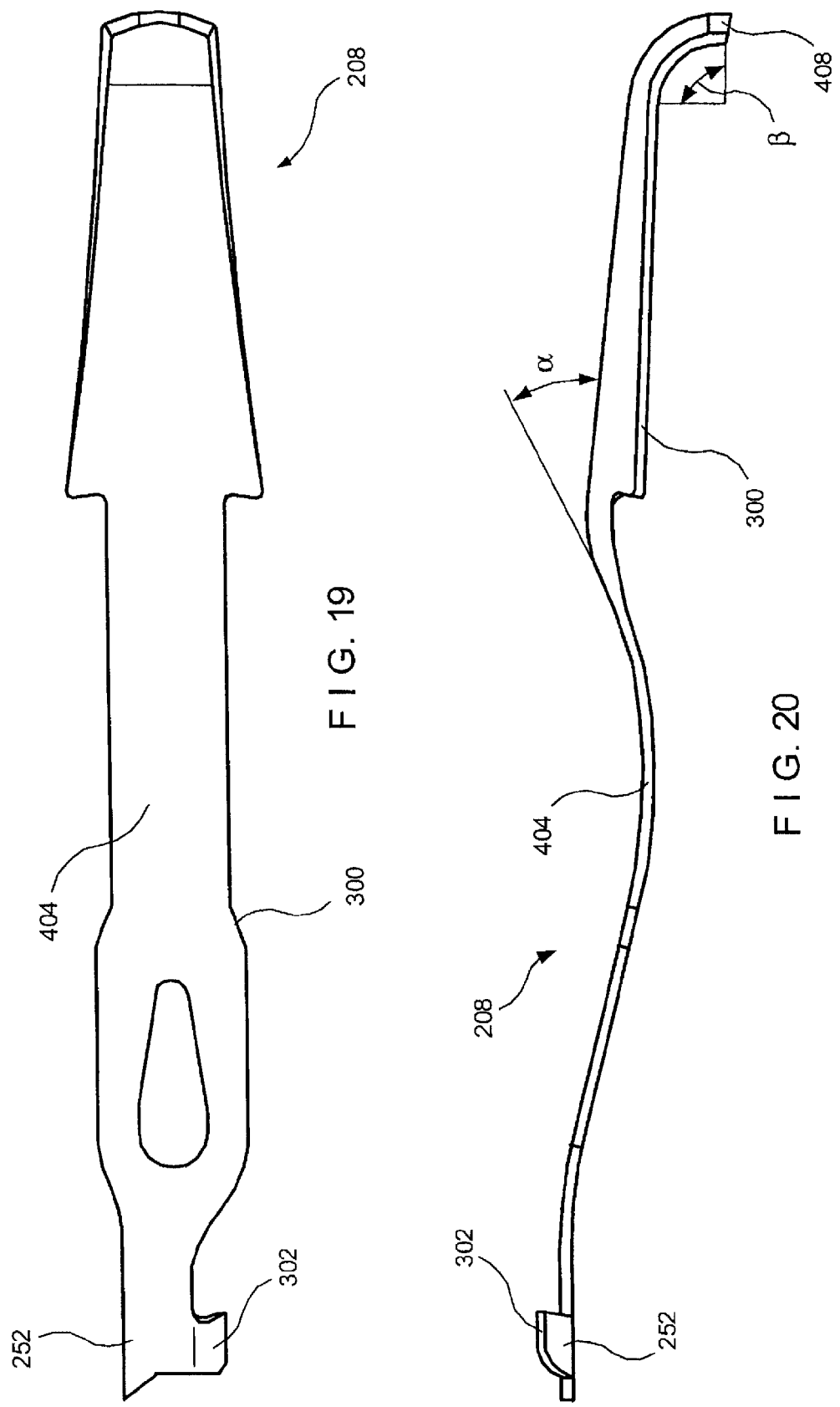

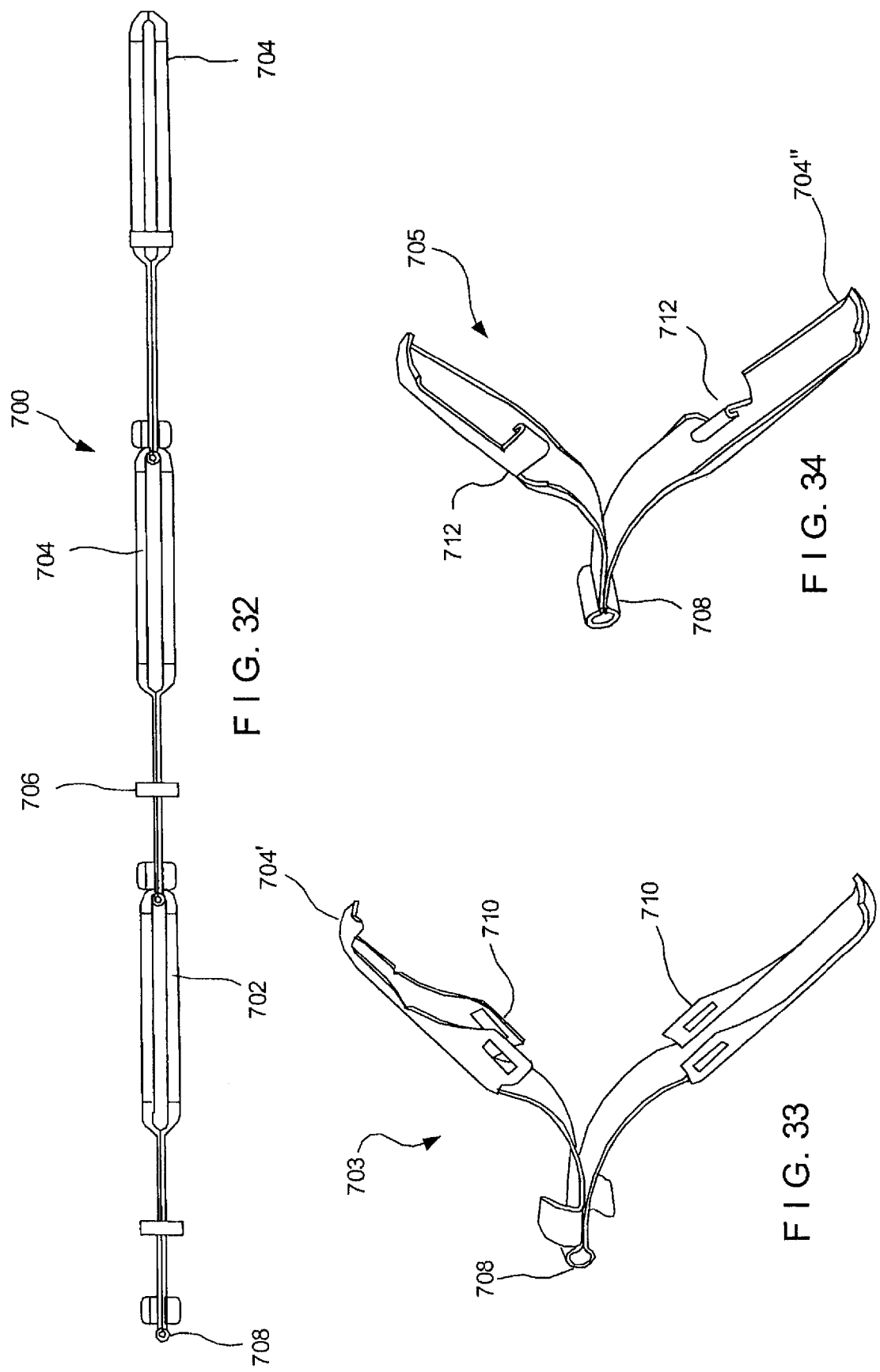

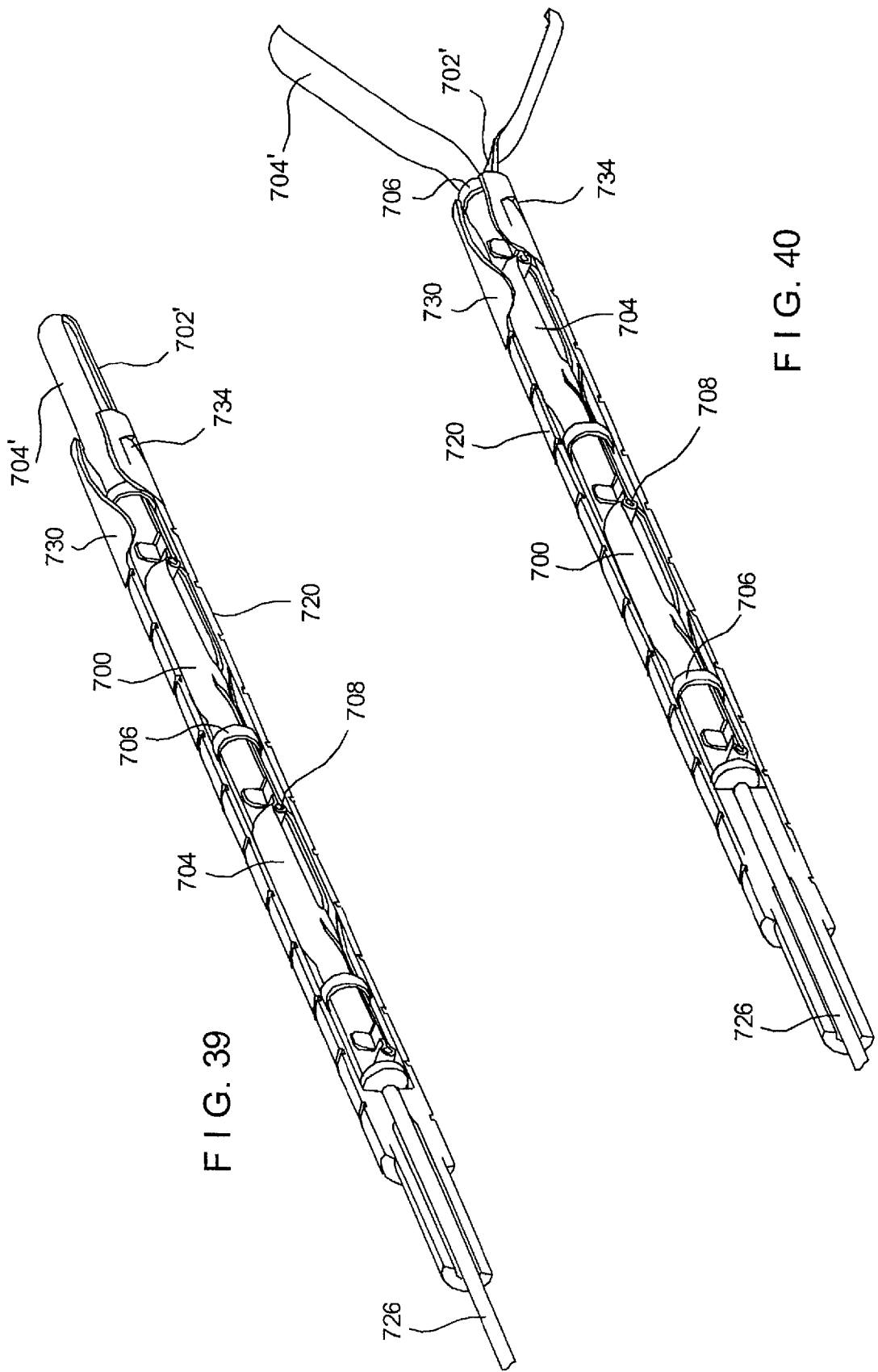

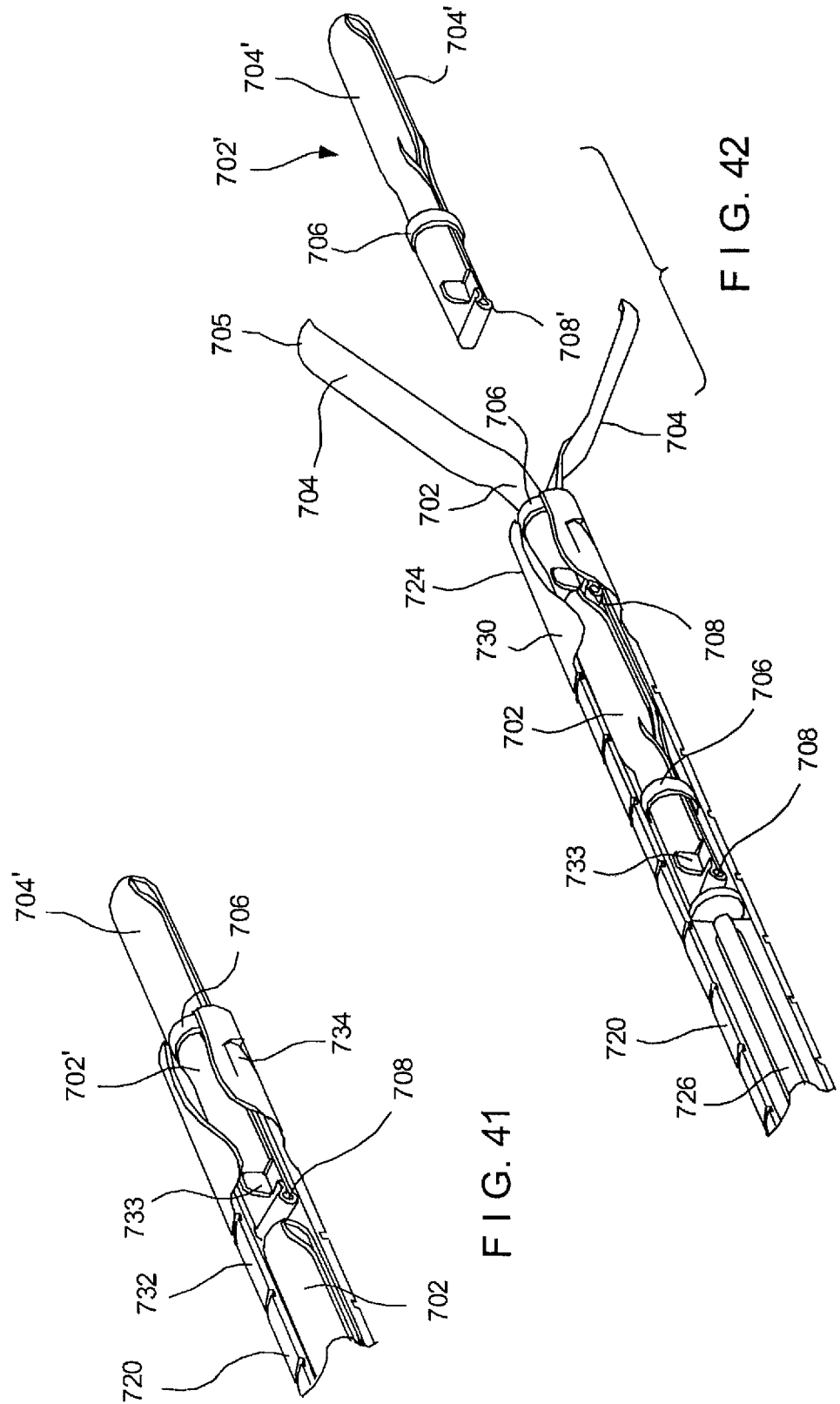

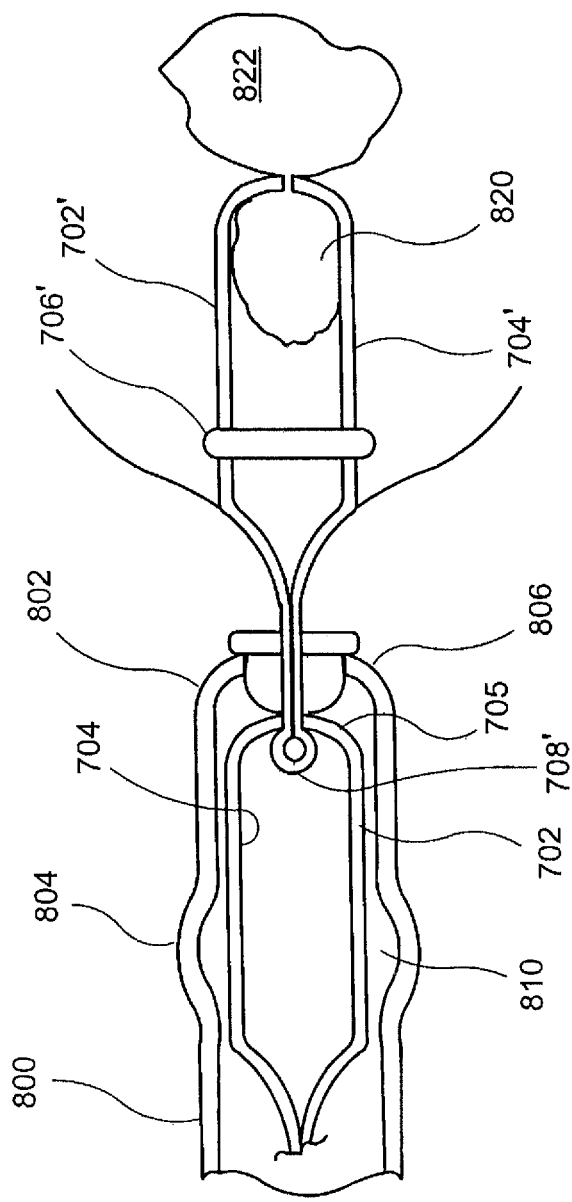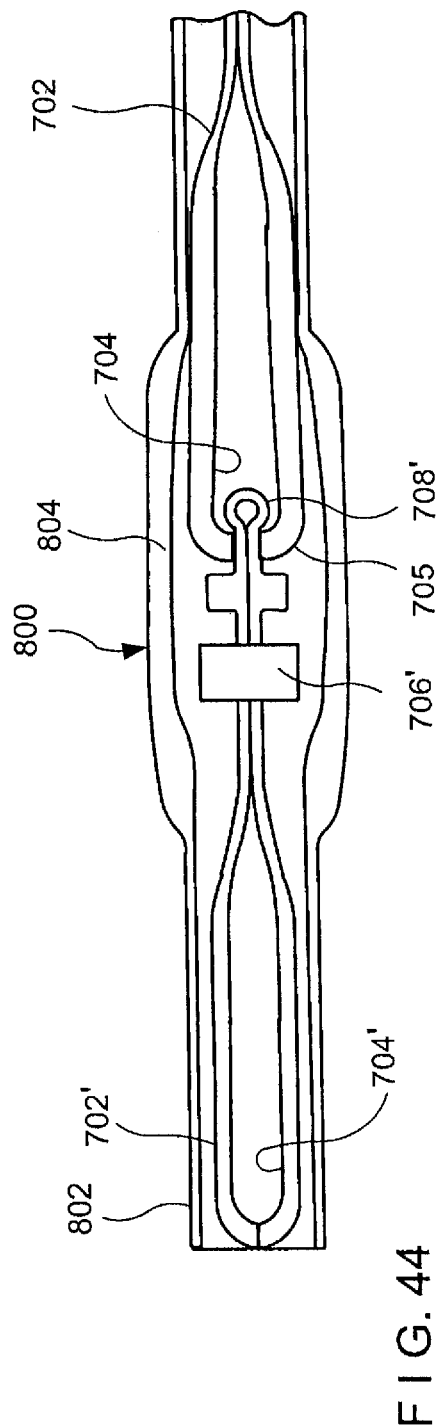
FIG. 43
FIG. 44

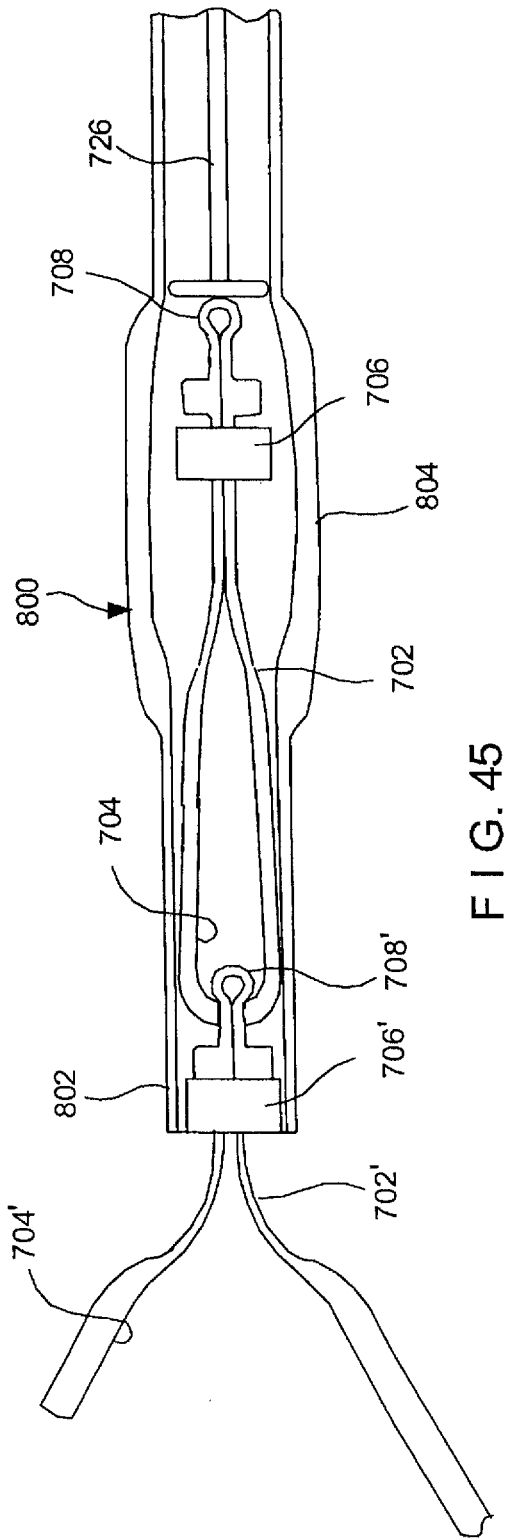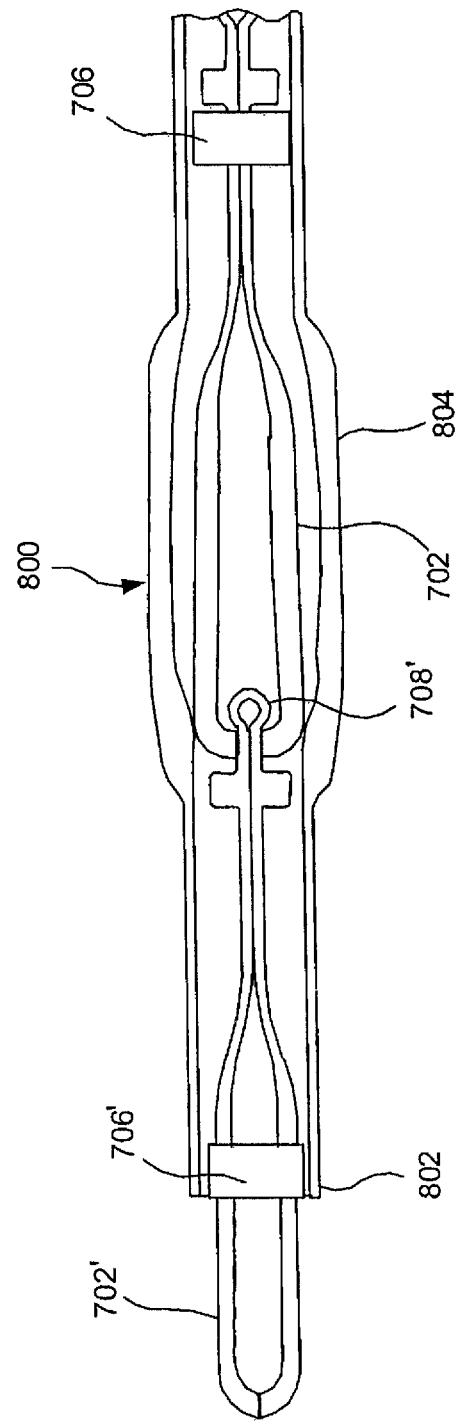
FIG. 45
FIG. 46

MULTIPLE CLIP DEPLOYMENT MAGAZINE

PRIORITY CLAIM

This application is a Continuation application of U.S. patent application Ser. No. 11/032,973 filed on Jan. 11, 2005 entitled "Multiple Clip Deployment Magazine". The application is expressly incorporated herein, in its entirety, by reference.

BACKGROUND

Endoscopic procedures to treat abnormal pathologies of the gastrointestinal ("GI") canal, of the biliary tree, of the vascular system and of various other body lumens are becoming increasingly common. An endoscope is basically a hollow tube placed at a desired location within the body to facilitate access to the relevant body ducts and lumens, etc. The endoscope itself cannot carry out many of the required procedures. To that end, the endoscope is fitted with a lumen, or internal channel, which permits the user to insert various medical devices therethrough to the location that requires treatment. Once the distal end of the inserted device has reached the tissue to be treated, it can be manipulated using controls which remain outside the body.

An hemostatic clipping tool is one of the devices which may be inserted through an endoscope so that treatment may be carried out. Hemostatic clips are deployed from the clipping tool and are used to stop internal bleeding by clamping together the edges of a wound. The clipping tool complete with clips attached to its distal end is inserted through the endoscope to the location of the bleeding. A clip is then remotely manipulated into position over the site of bleeding, clamped over the wound and detached from the tool. After a number of clips sufficient to stop the bleeding has been deployed, the tool is withdrawn from the patient's body through the endoscope. The size and shape of the clips and of the clipping tool are limited by the inner diameter of the endoscope's lumen, thus placing constraints on the design of the clip positioning and release mechanisms.

One challenge facing the endoscope operator is to properly position the hemostatic clips over the wound, so that closing the clips over the tissue will be effective in stopping the bleeding. If a clip is deployed improperly, additional clips may be required to stop the bleeding extending the time required for and the complexity of the procedure and leaving additional medical devices within the patient. It is thus beneficial if the clipping tool allows the user to orient the clips as required during deployment. It is also important for the device operator to be certain of the status of the clip during the deployment operation. For example, before withdrawing the tool from the endoscope, the operator should have positive indication that a clip has fully deployed, and has been released from the tool. At the same time the design of the tool should ensure that clips are fully released after they have been closed over the tissue.

SUMMARY OF THE INVENTION

In one aspect, the present invention is directed to an apparatus for deployment of multiple hemostatic clips, comprising a shaft connected to a handle and a control linkage operatively connected to the handle in combination with a magazine disposed at a distal end of the shaft, the magazine containing a plurality of clips arranged in a chain rotatable within the magazine, wherein a proximal-most one of the clips is coupled to the control linkage. A distal portion of the magazine is contoured to permit opening of a distal-most one of the clips during a distal stroke of the control linkage and to assist closing and locking of the distal-most clip during a proximal stroke of the control linkage. The magazine includes an expanded chamber sized to allow opening in any rotational orientation of a next clip located immediately proximal to the distal-most clip to a degree sufficient to disengage the distal-most clip from the clip chain.

The present invention is further directed to a method for deploying multiple hemostatic clips, comprising positioning a distal end of a magazine containing a clip chain over selected target tissue and actuating a control link of the magazine in a distal stroke to open and distally translate a distal-most clip of the clip chain in combination with orienting the open distal-most clip in a desired orientation to grasp the target tissue and actuating the control link in a proximal stroke to close and lock the distal-most clip over the target tissue. The control link is further actuated in the proximal stroke to move a next clip immediately proximal to the distal-most clip into an expanded portion of the magazine sized to allow the next clip to open to a degree sufficient to release the distal-most clip from the clip chain regardless of a circumferential orientation of the next clip and the distal-most clip is released by partially opening the next clip.

BRIEF DESCRIPTION OF THE DRAWINGS

FIG. 8 is a perspective view of an outer sheath lock according to an embodiment of the present invention;

FIG. 9 is a cross sectional side view of a distal end of a clipping device according to an embodiment of the present invention;

FIG. 10 is a cross sectional top view of a distal end of the clipping device shown in FIG. 9;

FIG. 15 is a cross sectional side view of the of the capsule shown in FIG. 14;

FIG. 16 is a top view of the distal end of a clipping device according to an embodiment of the present invention;

FIG. 17 is a side view of the distal end shown in FIG. 16;

FIG. 19 is a side view of the clip arm shown in FIG. 18;

FIG. 20 is a top view of the clip arm shown in FIG. 18;

FIG. 32 shows a side elevation view of a clip chain according to an embodiment of the invention;

FIG. 33 shows a perspective view of a second embodiment of a clip for a clip chain according to the invention;

FIG. 34 shows a perspective view of a third embodiment of a clip for a clip chain according to the invention;

FIG. 39 shows the clip chain of FIG. 38 being pushed out of the clip magazine;

FIG. 40 shows the clip chain of FIG. 38 yet further out of the clip magazine with one clip deployed;

FIG. 41 shows a distal end detail of the clip magazine shown in FIG. 39;

FIG. 42 shows the clip chain of FIG. 38 with a clip deployed and released from the clip chain;

FIG. 43 is a schematic diagram showing a detail of the magazine an clips according to an embodiment of the present invention;

FIG. 44 is a cut-away diagram showing two clips in the magazine in a pre-deployment configuration;

FIG. 45 is a cut-away diagram showing one of the clips shown in FIG. 44 with open clip arms;

FIG. 46 is a cut-away diagram showing one of the clips of FIG. 44 being locked in the closed configuration;

DETAILED DESCRIPTION

Hemostatic clips are used routinely to stop bleeding from openings created during surgery as well as wounds resulting from other trauma to tissues. In the simplest form, these clips grasp the tissue surrounding a wound and bring the wound's edges together, to allow the natural scarring process to heal the wound. Endoscopic hemostatic clips are used to stop internal bleeding due resulting from surgical procedures and/or tissue damage from disease, etc. Specialized endoscopic hemostatic clipping devices are used to bring the clips to the desired location within a patient's body and to position and deploy the clip at the appropriate place on the tissue. The clipping device is then withdrawn, leaving the clip within the patient. Such hemostatic clipping devices are described in U.S. patent application Ser. No. 10/647.512, filed on Sep. 30, 2003, and Provisional U.S. Patent Application Ser. No. 60/518,167 which are hereby incorporated herein by reference in their entirety.

Endoscopic hemostatic clipping devices are designed to reach affected tissues deep within a patient's body, such as within the GI tract, the pulmonary system, the vascular system or within other lumens and ducts. During the procedures to treat those areas, an endoscope is generally used to provide access to and visualization of the tissue which is to be treated. The clipping device may, for example, be introduced through a working lumen of the endoscope. The design and construction of such a "through the scope" endoscopic hemostatic clipping device presents several challenges. The endoscopic clipping device has to be sufficiently small to fit in the lumen of an endoscope and, at the same time, must be designed to provide for the positive placement and actuation of the hemostatic clip. Feedback to the operator is preferably also provided so that the operator will not be confused as to whether the hemostatic clip has been properly locked in place on the tissue and released from the device before the device itself is withdrawn through the endoscope.

Figure 1A:
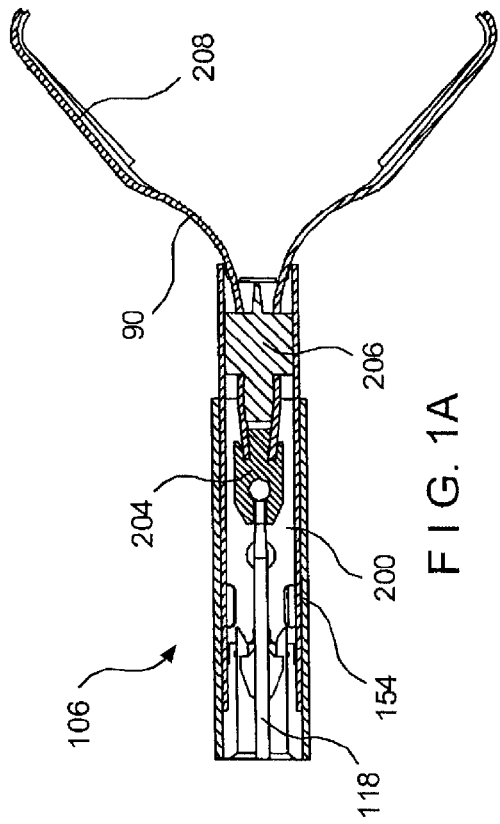
FIG. 1 is a schematic side view of a clipping device according to an embodiment of the present invention, with FIG. 1A showing a detail view of an exemplary clip assembly.
Figure 1:
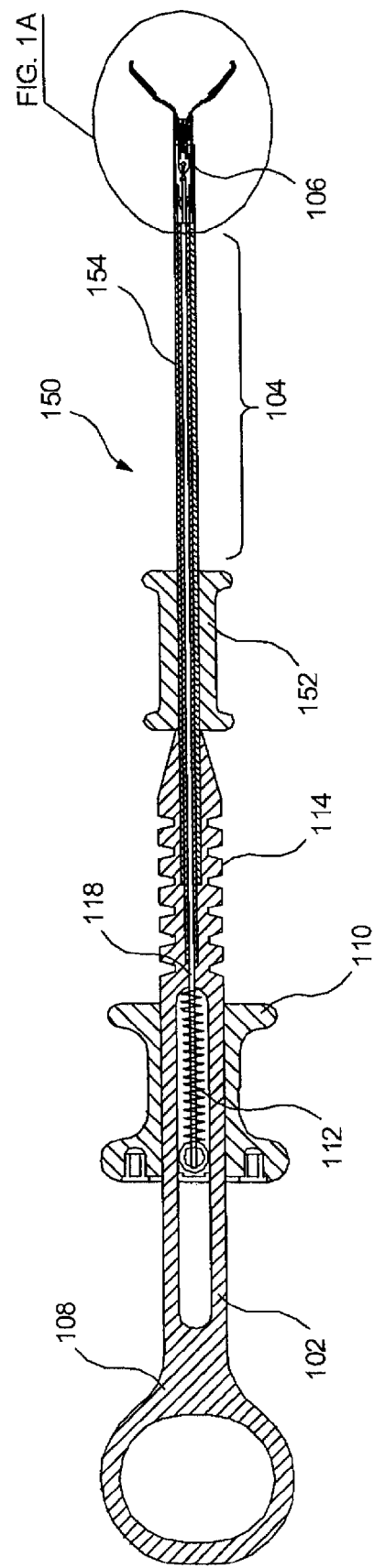

FIG. 1 shows a side elevation view of a through the scope hemostatic clipping device according to an exemplary embodiment of the present invention. This device is a hand operated tool that is used to insert a hemostatic clip through an endoscope lumen, position the clip over a wound, clamp it and deploy it over the affected tissue. The tool is further designed to release the hemostatic clip once it has been clamped in place, and to be withdrawn through the endoscope. To more clearly explain the operation and construction of the exemplary device, it may be divided into three principal components. As shown, the hemostatic clipping device 100 comprises a handle assembly 102, a shaft section 104, and a clip assembly 106. The clip assembly 106 is shown more clearly in FIG. 1A.

Handle assembly 102 forms the component that supplies a mechanical actuation force to deploy and clamp the clip. In this embodiment, the device is hand operated (i.e., the user's hands provide the force required to carry out all the functions related to the hemostatic clip). The handle assembly 102 may be constructed in a manner similar to conventional handle assemblies of the type generally employed in endoscopic biopsy devices or in similar applications. The handle assembly 102 allows the user to move a control wire 118 or other force transmission member, which extends through the shaft section 104 to the clip assembly 106 at a distal end of the device 100. The handle assembly 102 comprises a handle body 108 which can be grasped by the user to stabilize the device and apply a force to it. A sliding spool 110 is connected to control wire 118, so that the user can easily pull or push said wire 106 as desired.

Figure 2:
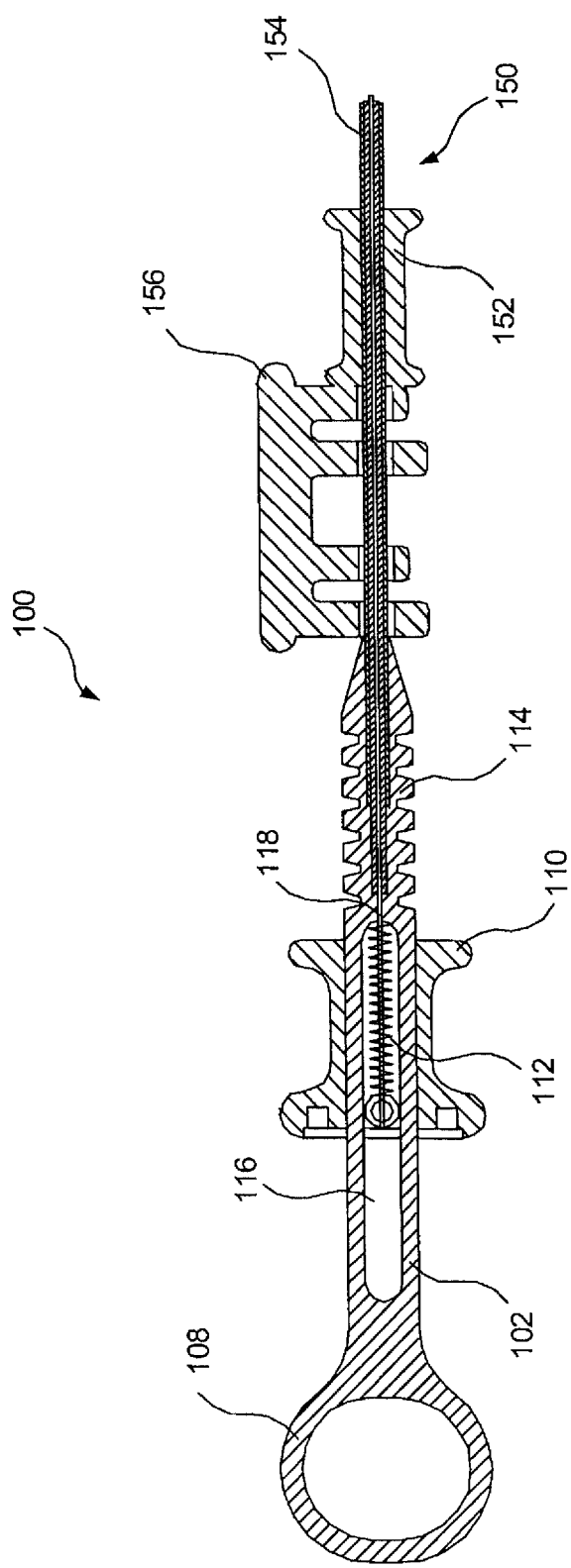
FIG. 2 is a schematic side view of the embodiment shown in FIG. 1, with a outer sheath.

As shown in FIGS. 1 and 2, a sliding spool 110 is mounted on the handle body 108 so that it can slide along a slot 116, which maintains its position within the handle assembly 102. Because the sliding spool 110 is connected to the control wire 118, the user may manipulate the control wire 118 by grasping the handle body 108 and moving the sliding spool 110 along the slot 116. A return spring 112 may be provided within the handle body 108 to bias the sliding spool 110, and thus the control wire 118 toward a desired position. In the present embodiment, the sliding spool 110 is biased to the proximal position. The handle assembly 102 may also include a connection portion 114, which receives the control wire 118 and attaches the shaft section 104 to the handle assembly 102.

Figure 4:
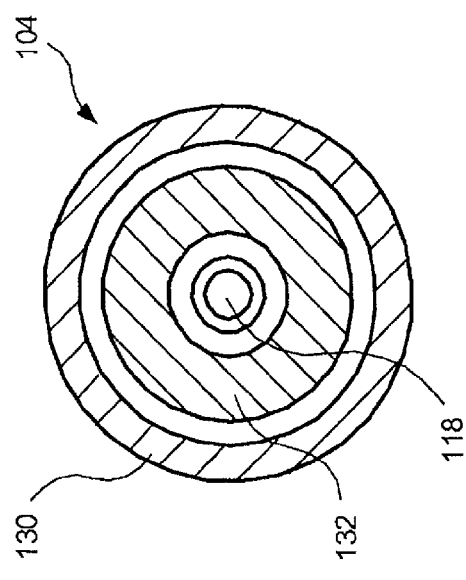
FIG. 4 is a cross sectional view of the shaft section shown in FIG. 3.
Figure 3:
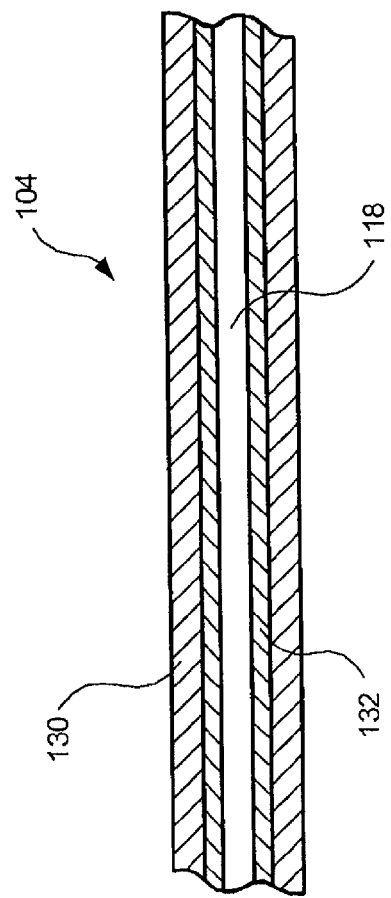
FIG. 3 is a cut away side view of the shaft section according to an embodiment of the present invention.

The shaft section 104 mechanically connects the handle assembly 102 to the clip assembly 106 and, together with the clip assembly 106, is designed to be inserted into a lumen of an endoscope. As shown in FIGS. 3 and 4, the shaft section 104 comprises an outer flexible coil 130 which is designed to transmit a torque from the proximal end to the distal end of the device 100 and to provide structural strength to the shaft section 104. The coil 130 may be a conventional coil used in biopsy devices and may, for example, comprise a single, coiled wire. The coiled wire may have a round, square or a rectangular cross section, and may be made of a biocompatible material such as, for example, stainless steel. Additional protective and low friction outer layers may be included on the shaft section 104, according to known methods of construction.

Figure 5:
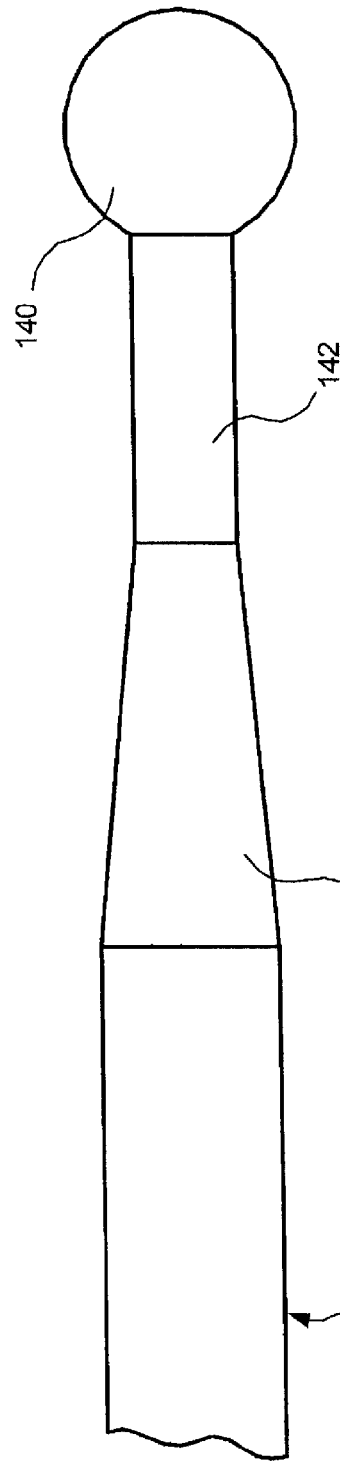
FIG. 5 is a detail view of the distal end of the control wire according to an embodiment of the present invention.

The control wire 118 transmits mechanical force applied to the handle 102 to the clip assembly 106. The control wire 118 has a proximal end which is attached to a movable part of the handle 102, such as the sliding spool 110, using known methods. Stainless steel or other high yield biocompatible materials may be used to manufacture the control wire 118, so that the structural integrity of the assembly is maintained. It is also important to prevent stretching of the control wire 118 when under tension since, if the wire stretches, the handle 102 will have to travel a greater distance to carry out a desired operation. As shown in FIG. 5, the distal end of the control wire 118 ends in a ball 140 which is used to connect the control wire 118 to the appropriate elements of the clip assembly 106, as will be described below. In this embodiment, the diameter of the control wire 118 is substantially constant from a proximal end thereof to a proximal end of a distal tapered section 144. The ball 140 may have a diameter which is greater than the diameter of the control wire 118, to facilitate attachment to a yoke 204. The control wire 118 may extend the length of the device 100, from the yoke 204 to the sliding spool 110, and may be designed to slide longitudinally along the device 100. It may be made, for example, of stainless steel or other biocompatible metal.

The control wire 118 may also include a reduced diameter section 142 designed to fail when a predetermined tension is applied thereto through the handle assembly 102. The tapered section 144 may be used to transition between the main body of the control wire 118 and the reduced diameter section 142, without steps or other discontinuities which may concentrate stress and make the fracture point more unpredictable. As will be described in greater detail below, one purpose of the reduced diameter section 142 is to facilitate the release of a hemostatic clip from the hemostatic clipping device 100 once the clip has been properly deployed. It will be apparent to those of skill in the art that the location of the reduced diameter section 142 the along control wire 118 may be varied to take into account specific requirements of the device 100.

An inner sheath 132 may be used in the construction of the shaft section 104, as shown in FIGS. 3 and 4. The inner sheath 132 provides a low friction bearing surface disposed between the outer diameter of the control wire 118, and the inner diameter of the shaft section 104. The inner sheath 132 may be formed of a low friction material such as, for example, Teflon™, HDPE or Polypropylene. In one exemplary embodiment, the inner sheath 132 is slidable within the shaft section 104, and the control wire 118 is slidable within the inner sheath 132 forming a low friction system of multiple bearing surfaces. To further reduce friction, a bio-compatible lubricant may be applied to the inner and outer surfaces of the inner sheath 132, along the length of the shaft section 104. For example, silicone lubricants may be used for this purpose.

A slidable over-sheath 150 may be included in the design of the shaft section 104, as shown in FIGS. 1 and 2. The over-sheath 150 is designed to protect the inner lumen of the endoscope from the metal clip assembly 106 and from the metal coil 130 while the hemostatic clipping device 100 passes through the endoscope's lumen. After the clipping device 100 and, more specifically, after the clip assembly 106 has passed through the endoscope, the over-sheath 150 may be withdrawn to expose the distal portion of the clipping device 100. The over-sheath 150 may be formed, for example, as a single lumen plastic extrusion element slidable over the distal portions of the clipping device 100 to selectively cover and uncover the clip assembly 106. In one embodiment, the over-sheath 150 is formed of a low friction polymer such as, for example, Teflon™, HDPE, Polypropylene, or similar materials.

The over-sheath 150 may include a grip portion 152 and an elongated body 154. The grip portion 152 is designed as a handle making it easier for the user to slide the over-sheath 150 over the shaft of the clipping device 100. In one exemplary embodiment, the grip portion 152 is made of a rubber-like material to provide a good gripping surface for the user. For example, an injection moldable polymer such as TPE may be used to construct the grip portion 152. The elongated body 154 may be formed as a substantially cylindrical shell surrounding the shaft of the clipping device 100. The elongated body 154 may be attached to the grip portion 152 using conventional methods as would be understood by those skilled in the art.

Figure 6:
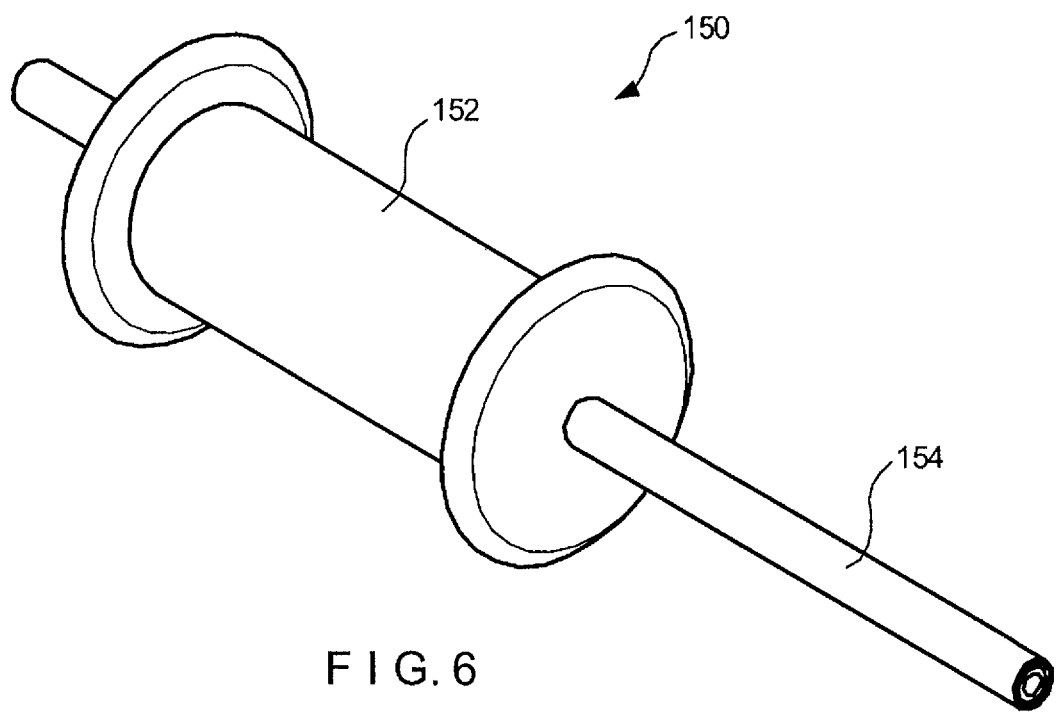
FIG. 6 is a perspective view of an outer sheath according to an embodiment of the present invention.
Figure 7:
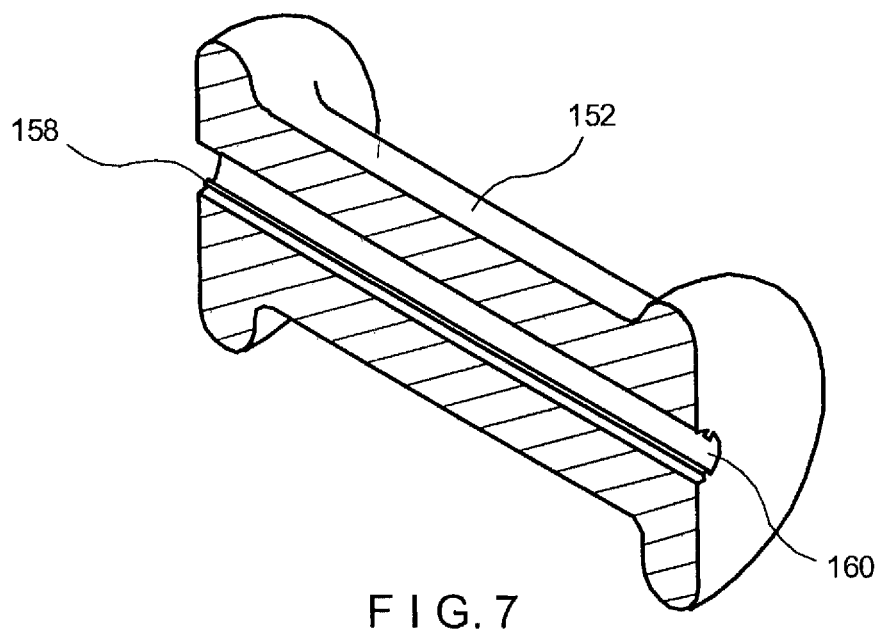
FIG. 7 is an cross sectional exploded view of the handle of the outer sheath shown in FIG. 6.

As shown in FIGS. 6 and 7, an exemplary grip portion 152 comprises a central hollow channel 160 that may be used to receive the shaft of the clipping device 100. The central hollow channel 160 is aligned with the elongated body 154 to provide a continuous channel containing the shaft of the clipping device 100. The material of the grip portion 152 may have a high coefficient of friction, so that an interference fit is possible between the central hollow channel 160 and the shaft of the clipping device 100 without the use of adhesives or mechanical fastening devices. In one embodiment, friction bosses 158 may be provided on an inner diameter of the hollow channel 160 to provide additional friction between the shaft of the clipping device 100 and the over-sheath 150 assembly. The friction bosses 158 may be formed, for example, as protrusions extending from the inner diameter of the over-sheath 150 and may have a variety of stubby or elongated shapes. The amount of friction between these two components may be balanced so that no unwanted relative movement takes place while, at the same time, making it relatively easy for the user to slide the over-sheath 150 proximally and distally when necessary.

A sheath stop 156 may be provided for the clipping device 100 to prevent the over-sheath 150 from sliding away from the distal end while the clipping device 100 is inserted in the endoscope. As shown in the exemplary embodiment of FIGS. 2 and 8, the sheath stop 156 physically blocks the grip portion 152 from sliding proximally to prevent the over-sheath 150 from being withdrawn and exposing the clip assembly 106. The sheath stop 156 is designed to easily snap in place near the proximal end of the shaft section 104 where it can be reached and manipulated by the operator during the surgical procedure. Once the clip assembly 106 has been inserted in the endoscope and has reached the desired location in the patient's body, the sheath stop 156 may be removed from the shaft section 104 so that the user can move the grip portion 152 proximally to uncover the clip assembly 106.

The connection between the sheath stop 156 and the shaft section 104 may include, for example, pairs of opposing fingers 162, 164 that are designed to snap over the shaft section 104. The fingers 162, 164 cooperate to securely and releasably hold the body of the shaft section 104 therebetween. The fingers 162, 164 respectively comprise guide portions 170, 172; shaft channel portions 166, 168; and blocking portions 174, 176. Insertion of the sheath stop 156 on the elongated body 154 is accomplished by pressing the body of the shaft section 104 between the guide portions 170, 172, to spread the fingers 162, 164 and allow further insertion of the shaft 104 between the fingers 162, 164. The guide portions 170, 172 and the blocking portions 174, 176 are shaped so that insertion of the shaft section 104 towards the channel portions 166, 168 requires less effort than moving the shaft section 104 in the opposite direction.

Once shaft section 104 has been placed within the channel portions 166, 168, the fingers 162, 164 snap back to their non-spread position and retain the shaft section 104 in place therebetween. The shaft section 104 is removed by pulling the sheath stop 156 away from the shaft section 104. Due to the shape of the blocking portions 174, 176, removing the shaft section 104 requires the application of more force than does insertion thereinto. Stops 180 may also be provided on the sheath stop 156 to limit the movement of the shaft section 104 towards the grasping portion 161 to prevent damage to the device that may be caused by excessive spreading of the fingers 162, 164. The sheath stop 156 may be formed of a resilient material, such as a polymer, and may be manufactured by injection molding.

Figure 11:
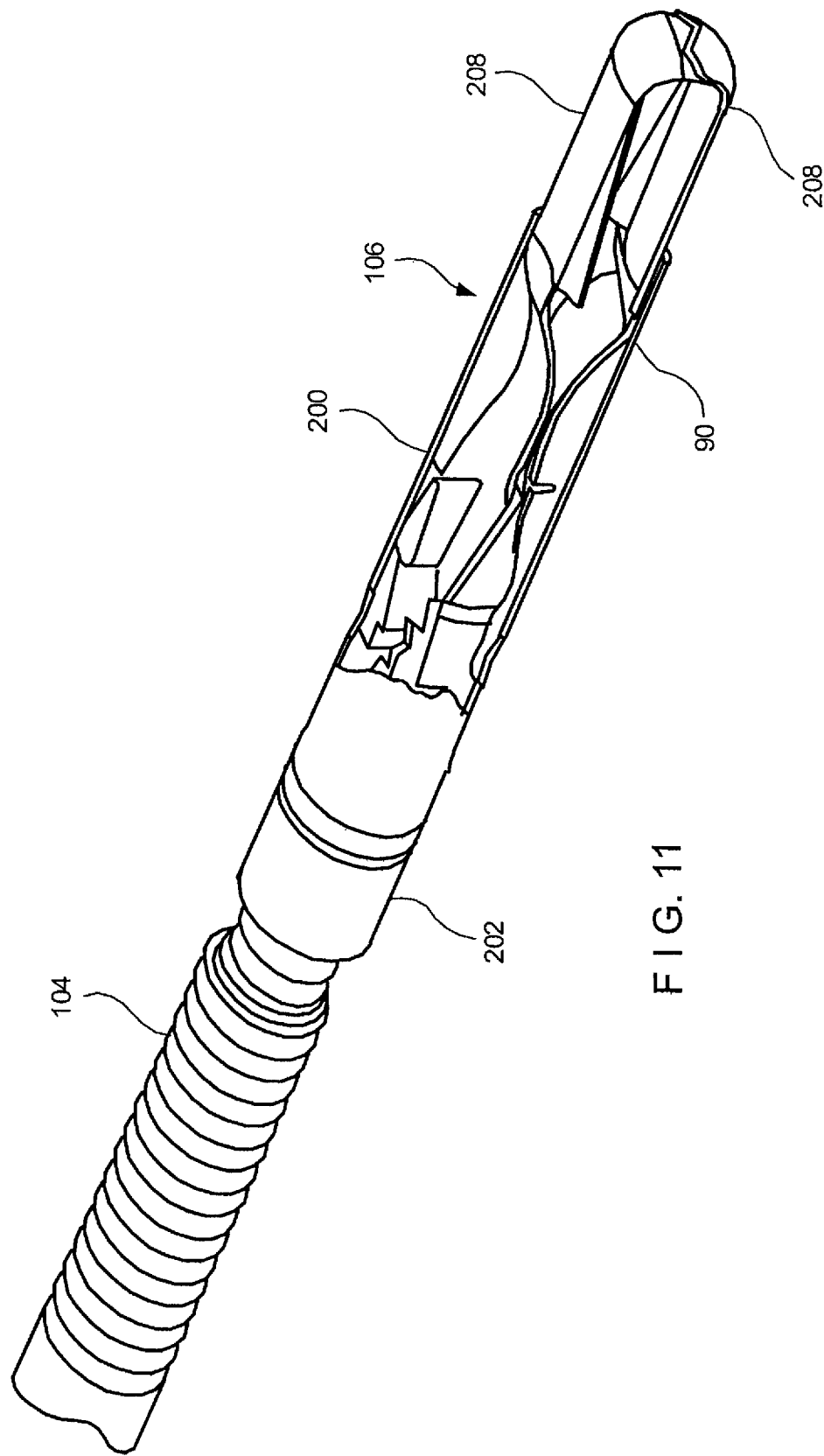
FIG. 11 is a perspective view of the distal end of the clipping device shown in FIG. 9.

The clip assembly 106 is disposed at the distal end of the clipping device 100, and contains the mechanism that converts the proximal and distal movement of the control wire 118 into the actions necessary to deploy and release a hemostatic clip 90. FIGS. 9, 10 and 11 show, respectively, side, top and perspective views of the distal end of the clipping device 100, including the clip assembly 106 having clips in the folded configuration. This configuration is used, for example, to ship the clipping device 100 and to insert the clipping device 100 through the lumen of an endoscope. Some of the components of the clip assembly 106 include a capsule 200 which provides a structural shell for the clip assembly 106, the clip arms 208 which move between open and closed positions, a bushing 202 attached to the distal end of the control wire 118, and a yoke 204 adapted to connect the capsule 200 to the control wire 118.

As depicted, the proximal end of the capsule 200 slides over the distal end of the bushing 202. A locking arrangement between these two components is provided by capsule tabs 212, which are designed to lock into the bushing 202 so that mechanical integrity is temporarily maintained between the capsule 200 and the bushing 202. Within the capsule 200 are contained a yoke 204 and a tension member 206 which transmit forces applied by the control wire 118 to the clip arms 208. The ball 140 formed at the distal end of the control wire 118 is mated to a receiving socket 210 formed at the proximal end of the yoke 204. A male C-section 214 extending from the tension member 206 is received in a corresponding female C-section 216 formed in the yoke 204, so that the two components are releasably connected to one another, as will be described below. The clip arms 208 in the closed configuration have a radius section 300 which is partially contained within the capsule 200 to prevent opening of the arms. Each of the clip arms 208 goes over the tension member 206 and has a proximal end 222 which slips under a yoke overhang 254, to further control movement of the arms 208.

Figure 12:
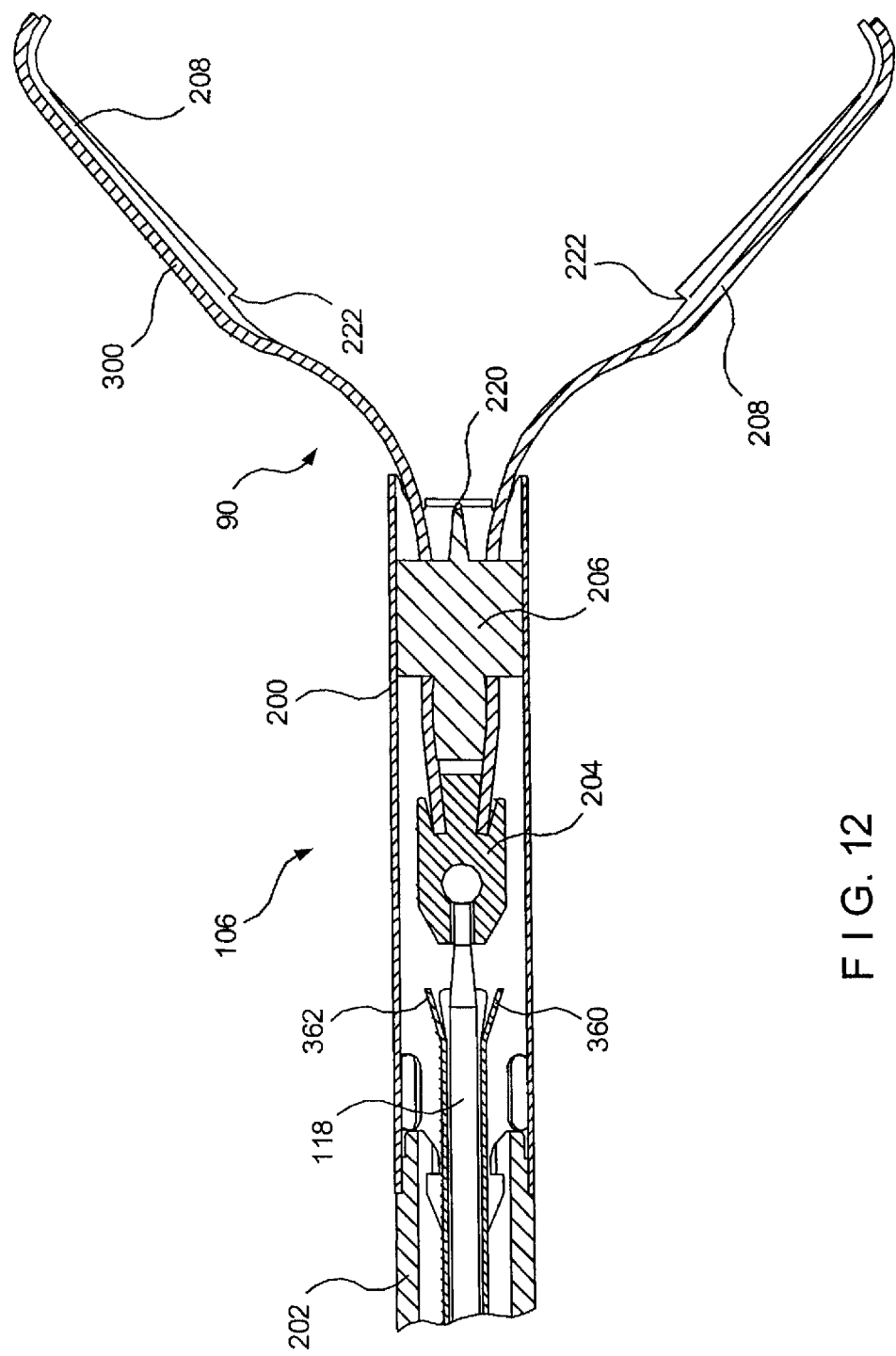
FIG. 12 is a top view of the clip arms according to an embodiment of the present invention.
Figure 13:
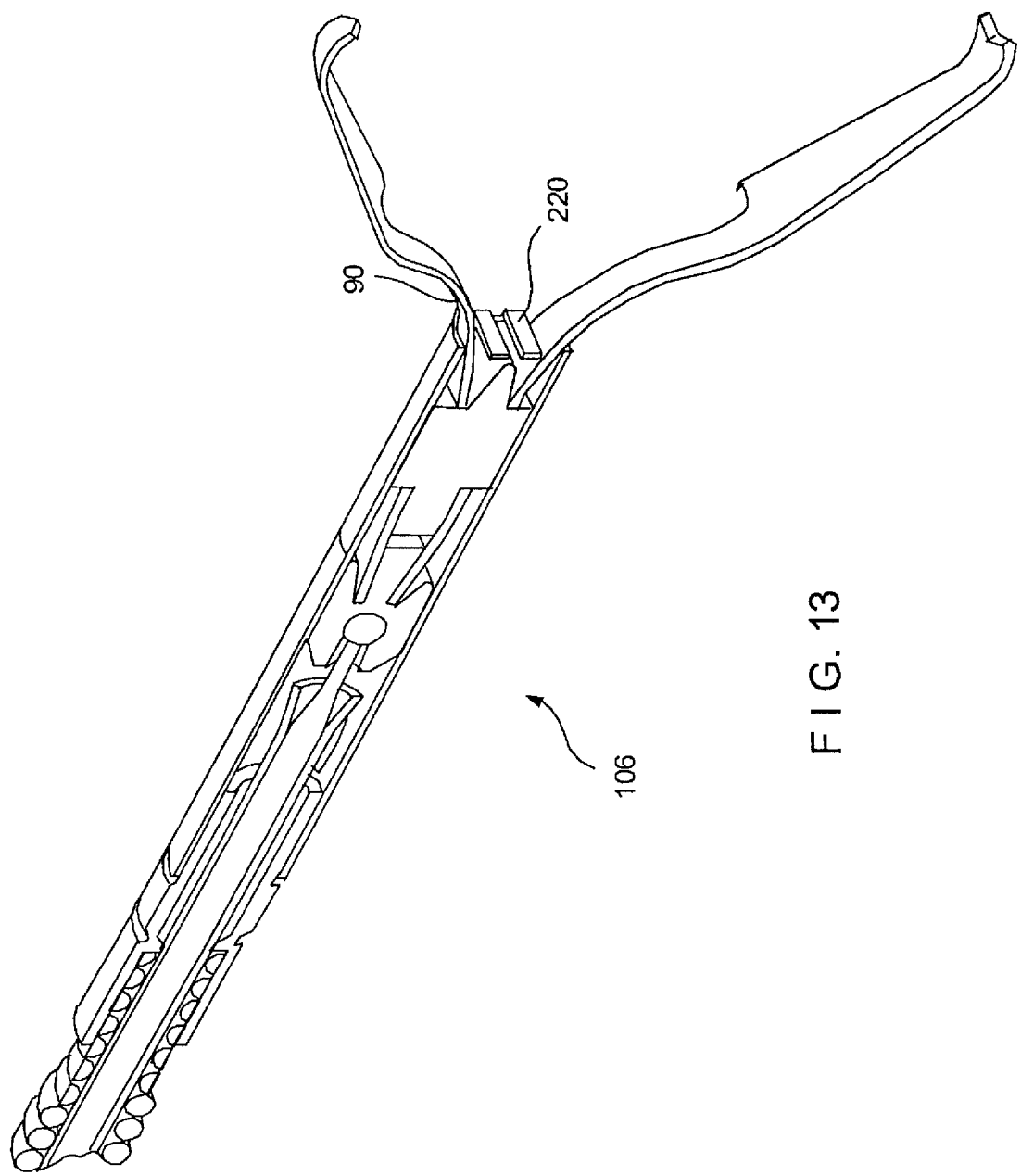
FIG. 13 is a perspective view of the clip arms shown in FIG. 12, according to an embodiment of the present invention.
Figure 14:
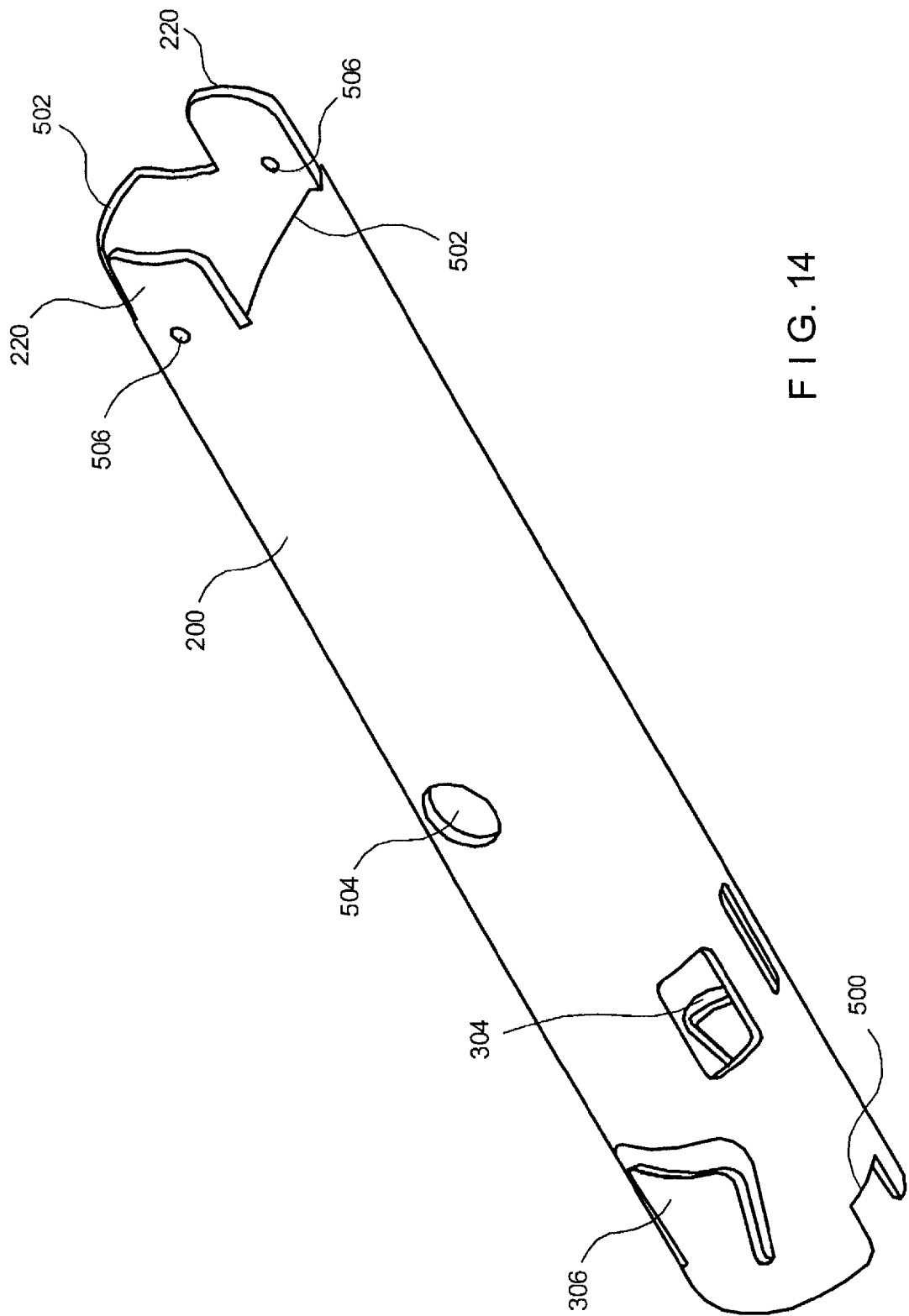
FIG. 14 is a perspective view of a capsule according to an embodiment of the present invention.

FIGS. 12 and 13 show a top and a perspective view of one exemplary embodiment of the clip assembly 106 in an open configuration with the clip arms 208 in a fully open position. The open configuration is obtained when the sliding spool 110 shown in FIG. 1 is moved distally so that the ball 140 of the control wire 118 pushes the assembly containing the yoke 204 and the tension member 206 forward, sliding within the capsule 200. As will be described below, the distal ends of the clip arms 208 are biased toward the open position and revert to this position whenever they are not constrained by the capsule 200. In the exemplary embodiment, a maximum opening of the clip arms 208 occurs when the clip arms 208 ride over the folded distal folding tabs 220 which extend from the distal end of the capsule 200, as shown in FIGS. 14 and 15. In this embodiment, the tabs 220 provide a cam surface, and the clip arms 208 act as cam followers, being deflected by the tabs 220. In addition, the folding tabs 220 may also provide a distal stop for the tension member 206, to retain it within the capsule 200. Thus, by moving the sliding spool 110 distally, the user opens the clip arms 208 to prepare to grasp tissue therebetween.

When the sliding spool 110 is moved proximally by the user, the assembly within the capsule 200 also moves proximally and the clip arms 208 are withdrawn within the capsule 200. As the clip arms 208 move proximally within the capsule 200, clip stop shoulders (CSS) 222 contact a distal portion of the capsule 200, for example, the folded tabs 220. This interaction of the CSS 222 with the capsule 200 provides to the user a first tactile feedback in the form of increased resistance to movement of the sliding spool 110. This feedback gives to the operator a positive indication that further movement of the handle control will cause the hemostatic clip 90 to be deployed from the clip assembly 106. The operator may then decide whether the current position of the clip 90 is acceptable or not. If the position is acceptable, the operator can deploy the clip 90 by continuing to move the sliding spool 110 with increased proximal pressure to cause the clip arms 208 to close on the tissue. If not, the operator can move the sliding spool 110 distally to re-open the clip arms 208 and extend them out of the capsule 200, reposition the clip 90, and repeat the above steps to close the clip 90 at a more appropriate location.

When the user determines that the clipping device 100 is positioned correctly, the proximal pressure on the sliding spool 110 may be increased to continue deployment of the hemostatic clip 90 from the clip assembly 106. FIGS. 16 and 17 show respectively a top and side view of the clipping device 100 in this condition. As the proximal tension on sliding spool 110 is increased, the control cable 118 pulls the yoke 204 proximally, away from the tension member 206. The tension member 206 is firmly attached to the clip arms 208 which are prevented from moving proximally by the interaction of the CSS 222 with the folded tabs 220. If sufficient pulling force is applied to the yoke 204, the male C section 214 of the tension member 206 yields and loses integrity with the female C section 216 of the yoke 204. This can occur because, in the exemplary embodiment, the tension member 206 is formed of a material with a lower yield strength than the material of the yoke 204.

The force required to break the tension member 206 away from the yoke 204 may be tailored to achieve a desired feedback that can be perceived by the user. The minimum force required to break the tension member 206 free of the yoke 204 may be selected so that a tactile feedback is felt by the user, to prevent premature deployment of the hemostatic clip 90 while a maximum force may be selected so that other components of the linkage between the sliding spool 110 and the clip arms 208 do not fail before the male C section 214 and the female C section 216 disconnect from one another. In one exemplary embodiment, the tension force necessary to disconnect the two components may be in the range of approximately 4 lbf to about 12 lbf. This range may vary depending on the size of the device and the specific application. To obtain this force at the interface of the male and female C sections 214, 216 a larger force will be applied by the user at the sliding spool 110, since friction within the device may cause losses along the long flexible shaft.

Figure 18:
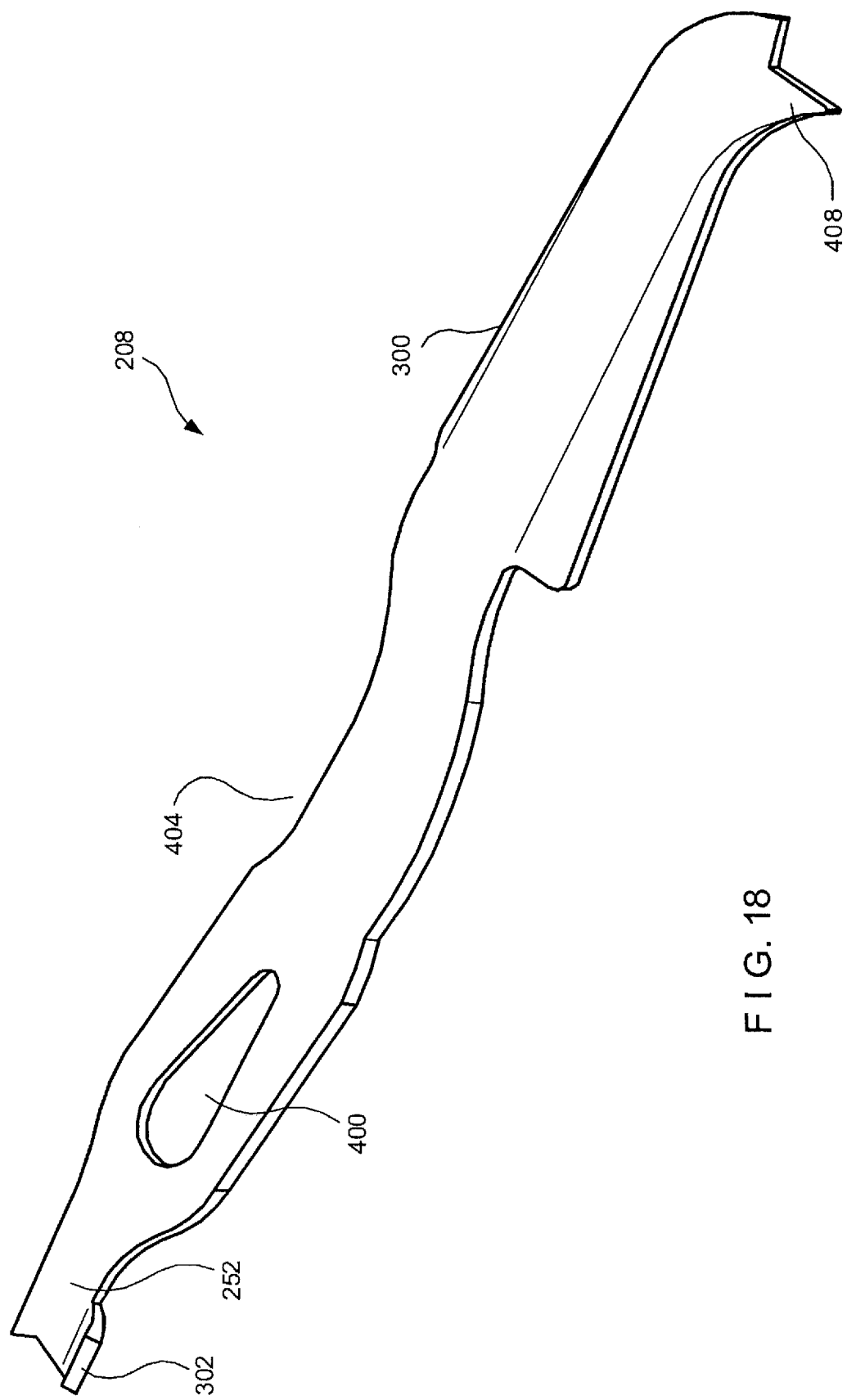
FIG. 18 is a perspective view of a clip arm according to an embodiment of the present invention.

When the male C section 214 of tension member 206 yields, several events take place within the exemplary device 100 nearly simultaneously. More specifically, the yoke 204 is no longer constrained from moving proximally by the CSS 222 abutting the capsule 200. Thus the yoke 204 travels proximally until coming to rest against a distal bushing shoulder 250. The tension member 206 is not affected by this movement since it is no longer connected to the yoke 204. The proximal ends 252 of the clip arms 208 are normally biased away from a center line of the device 100 and are no longer constrained by the yoke overhangs 254. Accordingly, the clip latches 302 are free to engage the latch windows 304 of the capsule 200, thus maintaining the integrity of the capsule-clip arms combination after deployment. Details of one exemplary embodiment of the capsule 200 are shown in FIGS. 14, 15 and details of the clip arms 208 are shown in FIGS. 18, 19 and 20.

Figure 21:
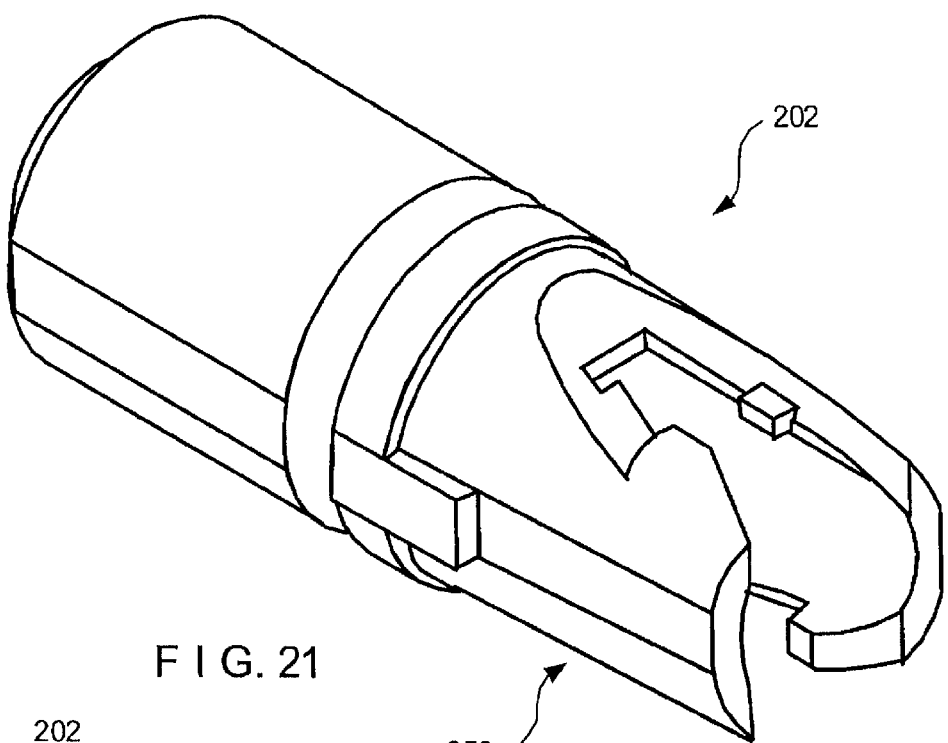
FIG. 21 is a perspective view of a bushing according to an embodiment of the present invention.

As the yoke 204 moves proximally to abut against the bushing 202, the capsule tabs 306 are bent away from the centerline of the capsule 200 by the cam surfaces of the yoke 204. As a result, the capsule tabs 306 are no longer engaged to the corresponding bushing undercuts 350, shown in the side and perspective views of the bushing 202 depicted in FIGS. 21, 22. Since the capsule 200 and the bushing 202 (which is securely connected to shaft section 104) are no longer connected, the clip assembly 106 is prevented from being released from the shaft section 104 only by its connection to the ball 140 of the control wire 118.

Figure 22:
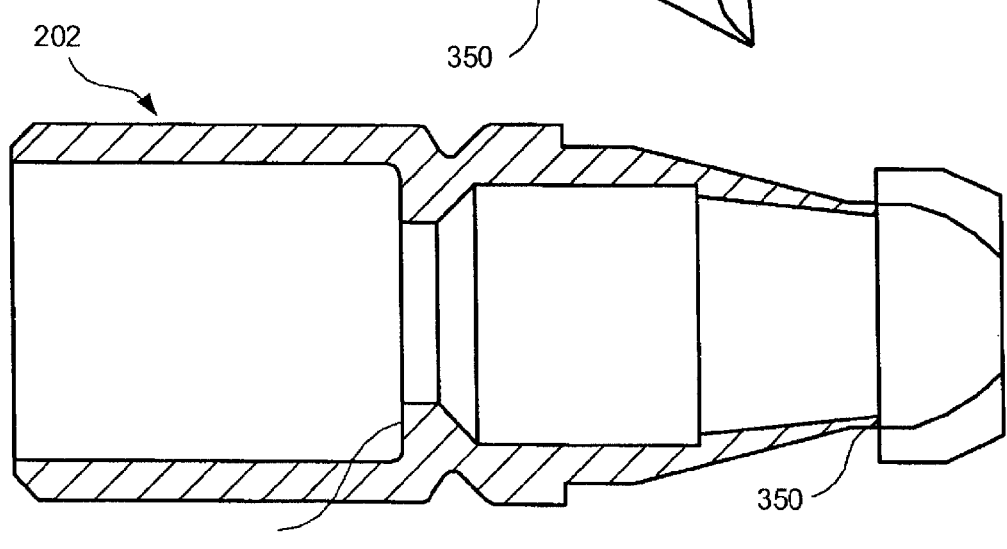
FIG. 22 is a cross sectional side view of the bushing shown in FIG. 21.
Figure 23:
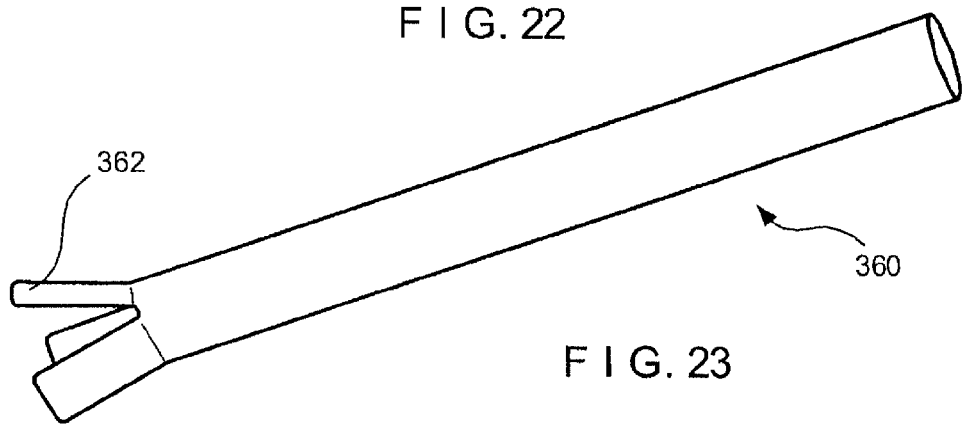
FIG. 23 is a perspective view of a wire stop according to an embodiment of the present invention.

A further result of moving the yoke 204 against the distal bushing shoulder 250 of the bushing 202 is that the distal end of the wire stop 360 (shown in FIGS. 12, 16) is placed near the proximal bushing shoulder 364 (shown in FIG. 22). The flared fingers 362 located at the distal end of the wire stop 360, better shown in FIG. 23, are compressed as they pass through the central ID of the bushing 202, but return to their normally biased open position (shown in FIG. 23) after passing past the proximal bushing shoulder 364. Further distal movement of the sliding spool 110 is thus prevented since that movement would engage the fingers 362 of the wire stop 360 with the proximal bushing shoulder 364. This feature prevents the clip assembly 106 from being pushed away from the bushing 202 before the ball 140 is separated from the control wire 118, as will be described below.

The wire stop 360 comprises a tube with a first slotted and flared end attached to the control wire 118 by conventional means. As shown in FIG. 23, the slots impart flexibility to the device so it can easily pass through the central lumen of the bushing 202. Flared fingers 362 are formed by the slots, and engage the proximal bushing shoulder 364. The wire stop 360 is made of a material that is biocompatible and that has enough resilience so that the fingers 362 re-open after passage through the bushing 202. For example, stainless steel may be used for this application.

One feature of the exemplary embodiment of the invention described above is that the user receives both tactile and auditory feedback as the clip assembly 106 is deployed and released. The separation of the tension member 206 from the yoke 204 produces a small clicking noise and a tactile feel that is perceptible while holding the handle assembly 102. The change in axial position of the sliding spool 110 is thus augmented by the changes in resistance to its movement and by the clicking sound and feel through the start and stop of the movement. As a result the user is always aware of the status of the clip assembly 106, and the inadvertent deployment of a hemostatic clip 90 in an incorrect location is less likely. It will be apparent to those of skill in the art that the order of male and female connectors in the device may be reversed or changed without affecting the operation of the device.

Figure 24:
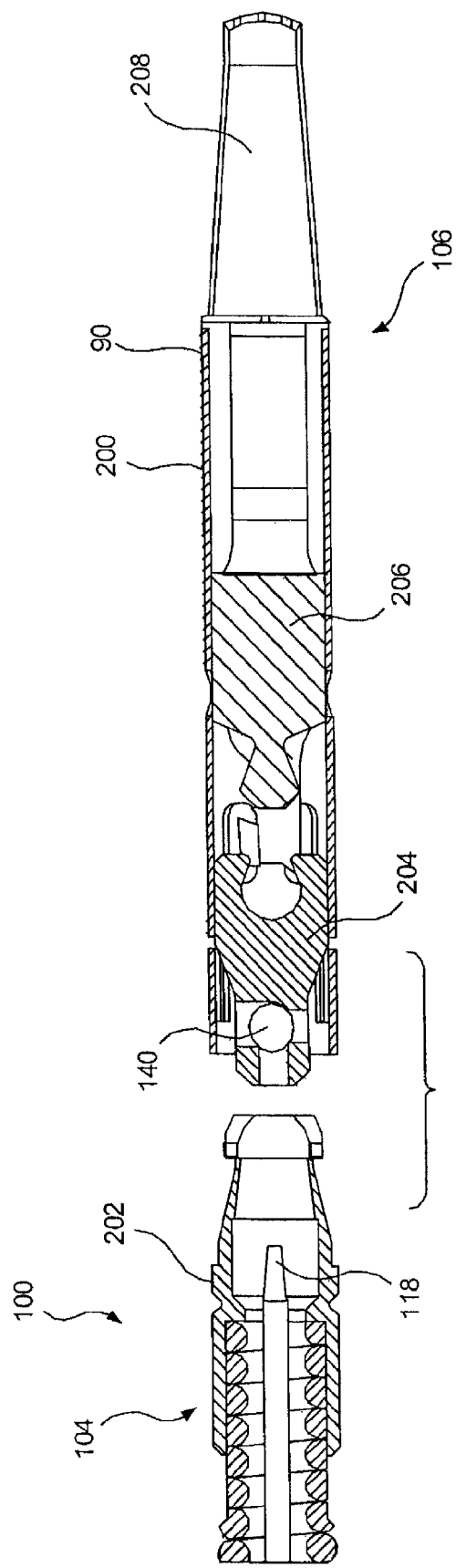
FIG. 24 is a schematic side view of a clip assembly detached from a bushing, according to an embodiment of the present invention.

It may be beneficial for the user to be certain that the clip assembly 106 has been deployed before the rest of the clipping device 100 is removed from the endoscope. Injury to the tissue being treated could result if the clipping device 100 is removed from the operative site when the hemostatic clip 90 is only partially deployed. Accordingly, a large tactile feedback may be incorporated, to augment the auditory and tactile feedback stemming from the separation of the yoke 204 from the tension member 206. FIG. 24 depicts the condition where the clip assembly 106 separates from the rest of the clipping device 100. According to the described embodiment, this second user feedback is obtained by designing the control wire 118 so that it will separate from the end ball 140 when a predetermined tension is applied to it. In other words, the ball 140 of the control wire 118 is mechanically programmed to yield and separate from the body of the control wire 118 when a pre-set tension is applied thereto. The size of the reduced diameter section 142 can be selected so that, when the user continues to move the sliding spool 110 proximally as the programmed yield tension is reached, the ball 140 detaches from the tapered section 144 and provides a large tactile feedback to the operator.

When the ball 140 detaches, the sliding spool 110 bottoms out at the proximal end of the handle 108, such that a full stroke of the handle assembly 102 is reached. The tension required to cause the reduced diameter section 142 to yield and release the ball 140 may vary over a range of values. However, for best results the force should be greater than the tension force required for the male C section member 214 to separate from the yoke 204. If this condition is not satisfied, a situation may occur where the clip assembly 106 is locked in place on the patient's tissue, but cannot be released from the clipping device 100. It will be apparent that this situation should be avoided. In one exemplary embodiment, the tension force required to separate the ball 140 from the body of the control wire 118 is in the range of between about 10 lbf and 20 lbf at the distal end of the control wire 118. As discussed above, losses along the elongated flexible shaft may require the user to apply a force substantially greater than this to the handle body 102.

Once the ball 140 has separated from the rest of the control wire 118, the user can pull the rest of the clipping device 100 from the endoscope. As this is done, the yoke 204 is retained within the capsule 200 by the spring and frictional forces of various features of the capsule 200, such as the capsule tabs 306. Prior to withdrawing the clipping device 100, the oversheath 150 may be moved distally by the user over the entire remaining portions of the shaft section 104 to prevent damage to the endoscope as the clipping device 100 is withdrawn therethrough. The sheath stop 156 may also be placed on the shaft section 104 proximally of the over-sheath grip 152 to prevent inadvertent sliding of the over-sheath 150 from the distal end of the device 100.

A more detailed description of several components of the clipping device 100 follows. The clip arms 208 are shown in detail in FIGS. 18, 19 and 20; the tension member 206 is shown in side and top views in FIGS. 25, 26; while top and side views of the yoke 204 are shown respectively in FIGS. 27 and 28. The clip arms 208 may be formed of a biocompatible material such as Nitinol, Titanium or stainless steel. Maximum spring properties may be obtained by using materials such as 400 series stainless or 17-7 PH. As shown, a tear drop keyway 400 is formed in the clip arm 208 to mate with a corresponding tear drop key 402 formed on the tension member 206. This feature maintains the relative positions of these two components and of the yoke 204 substantially constant. The shape of the keyways 400 may be varied. For example, the keyway 400 may be oval or elliptical. Central portions of the clip arms 208 define a spring section 404. When the proximal ends 252 of the clip arms 208 are under the yoke overhangs 254, the clip arms 208 are allowed to pivot over the tension member 206, which in turn biases the distal ends 252 towards the open configuration when no longer restrained by the capsule 200. As a result, the proximal end 252 of each clip arm 208 springs upward and engages the latch windows 304 in the capsule 200.

The clip arms 208 also comprise a radius section 300 that adds strength to the clip and reduces system friction. The radius of the radius section 300 approximately matches the inner diameter of the capsule 200 and has a smooth profile to avoid scratching the inner surface of the capsule 200. A pre-load angle α is defined between the radius section 300 and the spring section 404. The pre-load angle α determines how much interference (pre-load) exists between the two opposing clip arms 208 at their distal ends when closed. The greater the pre-load angle α, the greater the engaging force that is applied by the clip arms 208. However, this condition also causes the greatest system friction when the hemostatic clip 90 is closed. The clip arms 208 also comprise interlocking teeth 408 disposed at their distal ends. In the exemplary embodiment, the teeth 408 are identical so that the arms may be interchangeable and will mesh smoothly with the set facing them. The teeth 408 are disposed at a nose angle β which may be between approximately 90 and 135 degrees, but in other applications may be greater or lesser than the described range.

One exemplary embodiment of the capsule 200 is shown in detail in FIGS. 14 and 15 and comprises alignment keyways 500 that are designed to mate with corresponding features on the bushing 202 to rotationally align the two components. In this embodiment, the capsule tabs 306 may be bent towards the centerline of the capsule 200 to engage the bushing undercuts 350. The engagement maintains the integrity between the capsule assembly 200 and the rest of the clipping device 100 until the yoke is pulled into the distal bushing shoulder. The capsule overhangs 502 provide added clamping strength to the deployed clip arms 208. This is achieved by reducing the length of the portion of each clip arm 208 that is not supported by a portion of the capsule 200. This feature does not affect the amount of tissue that may be captured by the clip arms 208 since the capsule overhangs 502 extend on a plane substantially parallel to the plane of the clip arms 208.

Additional features of the capsule 200 include an assembly aid port which may be used to assist in aligning the components of the clip assembly 106. Bending aids 506 facilitate a smooth bend when the distal folding tabs 220 are bent inward, as described above. The bending aids 506, as shown, are holes aligned with the folding line of the tabs 220, but may also include a crease, a linear indentation, or other type of stress concentrator. The capsule 200 may be formed from any of a variety of biocompatible materials. For example, stainless steel, Titanium or Nitinol or any combination thereof may be used. High strength polymers like PEEK™ or Ultem™ may also be used to form the capsule 200, with a heat set treatment being used to adjust positionable elements.

Figure 26:
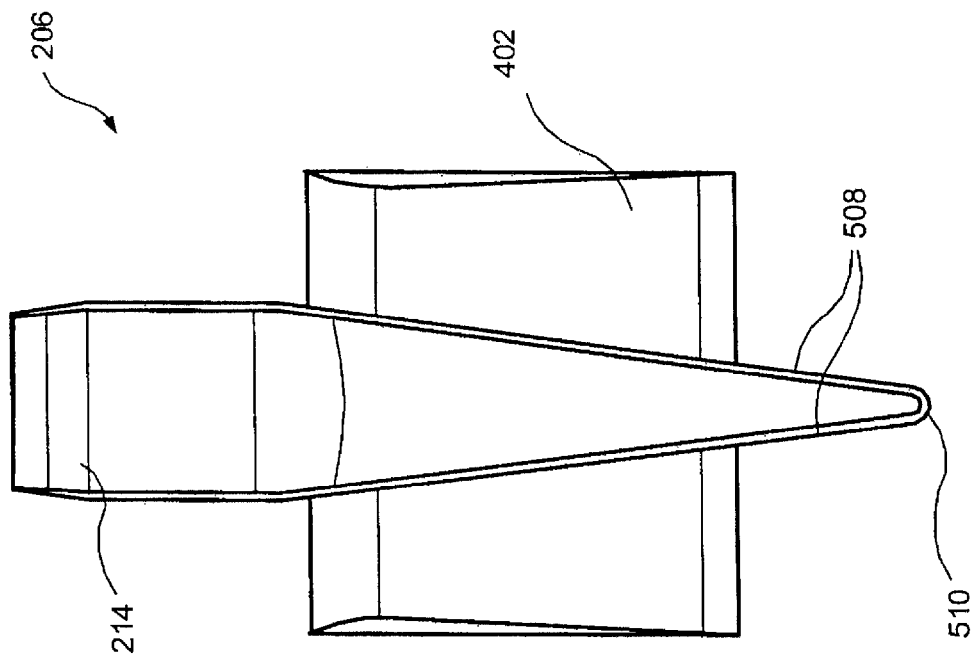
FIG. 26 is a top view of the tension member shown in FIG. 25.
Figure 25:
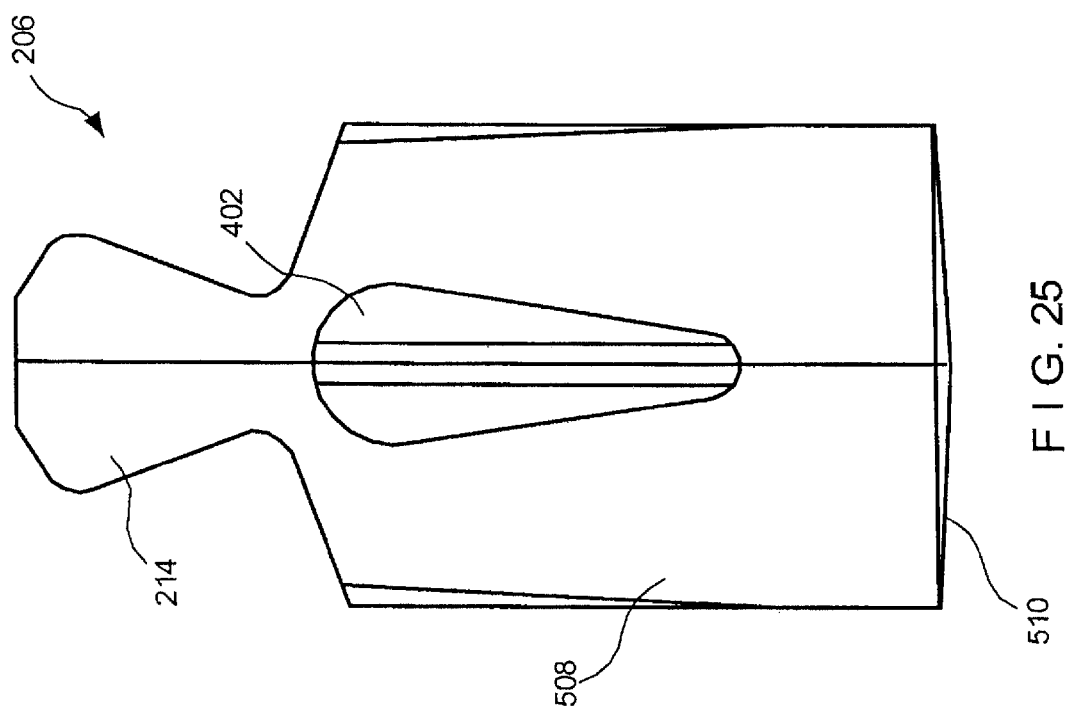
FIG. 25 is a side view of a tension member according to an embodiment of the present invention.

FIGS. 25 and 26 depict additional details of the tension member 206. As shown, tear drop keys 402 are designed to engage the tear drop keyways 400 of the clip arms 208, as described above. Clip follower planes 508 are shaped to form a fulcrum which allows the clip arms 208 to rock between the open and closed configurations. The tension member 206 comprises a distal stop face 510 which abuts the distal folding tabs 220 of the capsule 200 to stop the distal motion of the capsule assembly 106. In general, all surfaces and edges of the tension member 206 that are in contact with the inner surfaces of the capsule 200 preferably have a radius substantially similar to an inner radius of the capsule 200 to provide a sliding fit therein. The tension member 206 may be formed of a biocompatible polymer, monomer or thermoset. The type of mechanism selected to release the tension member 206 from the yoke 204 may determine the type of material used since a release due to fracture of the male C section 214 requires a relatively brittle material while release due to yielding without fracture calls for a softer material.

Figure 27:
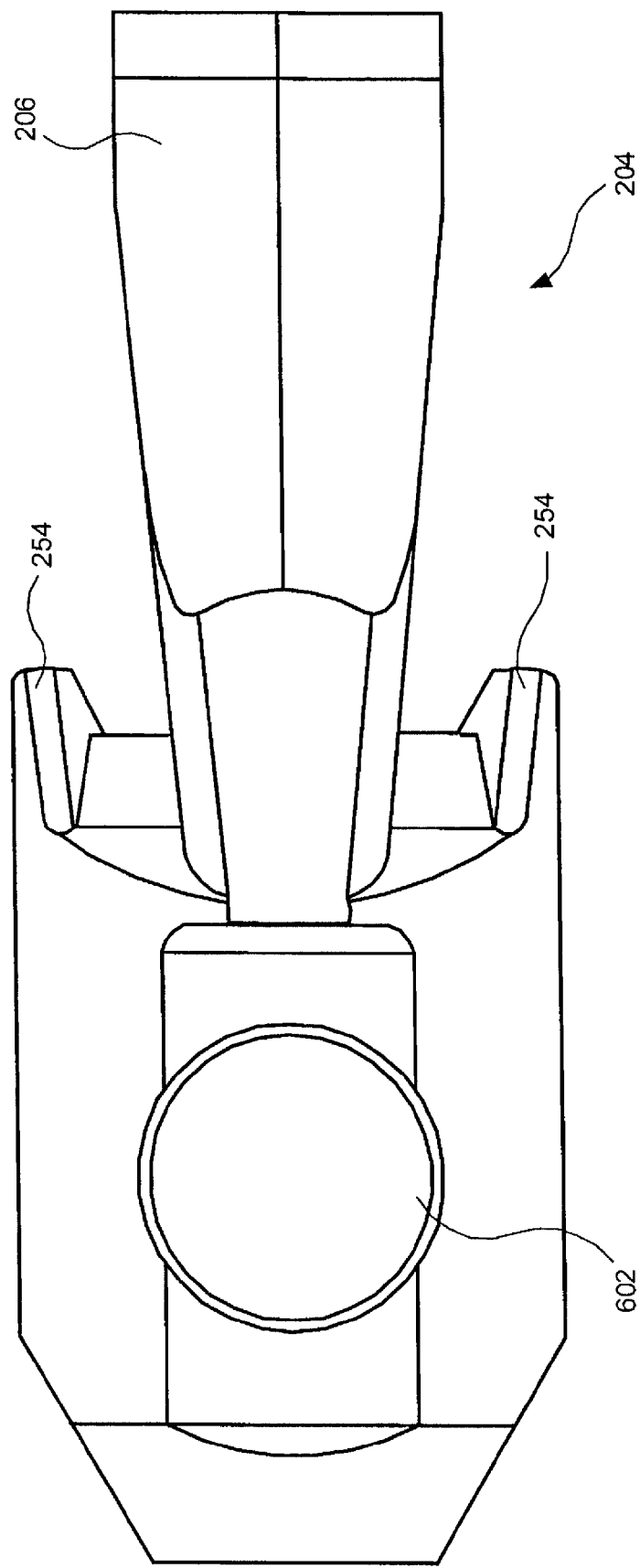
FIG. 27 is a top view of a yoke according to an embodiment of the present invention.
Figure 28:
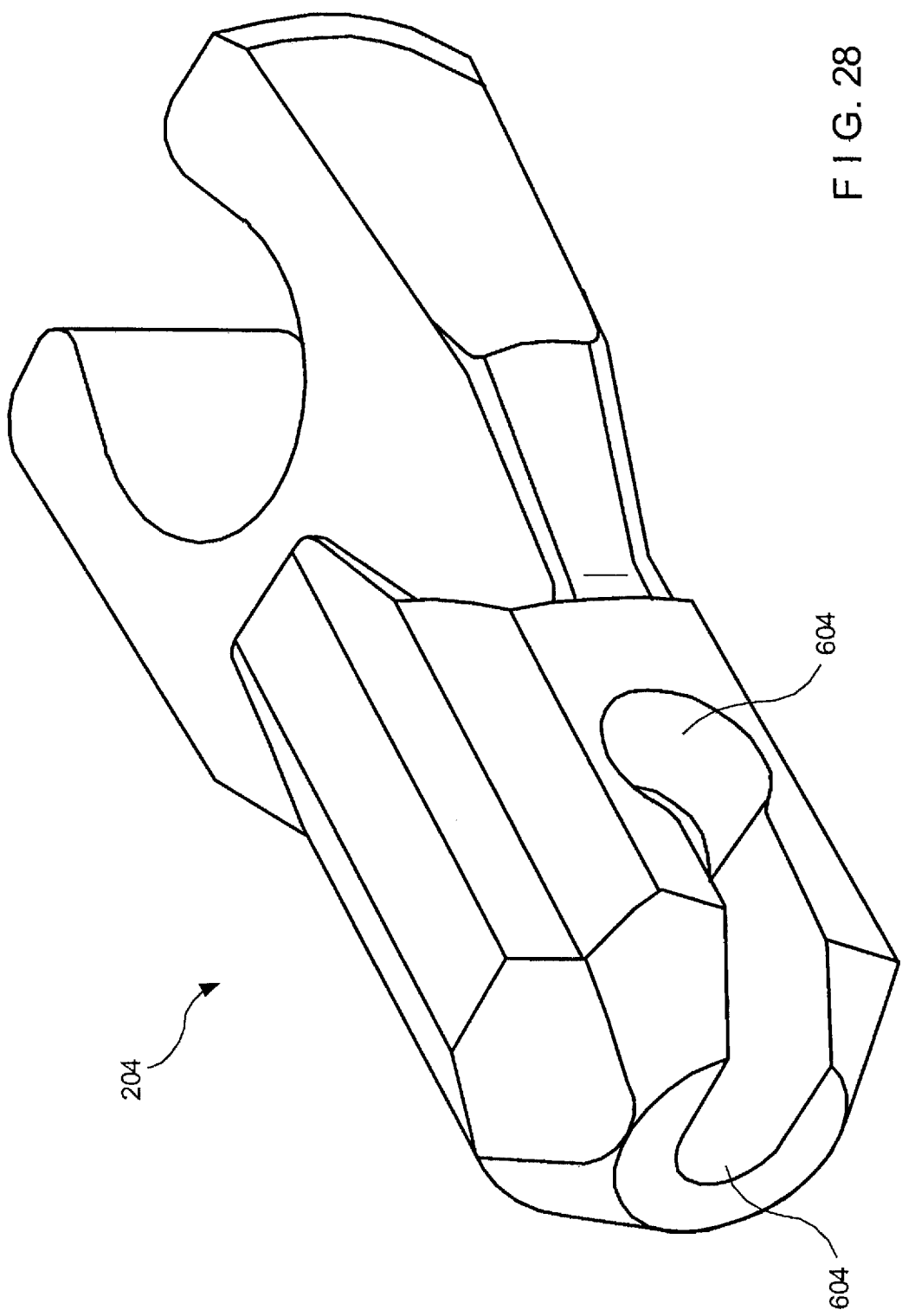
FIG. 28 is a perspective view of the yoke shown in FIG. 27.
Figure 29:
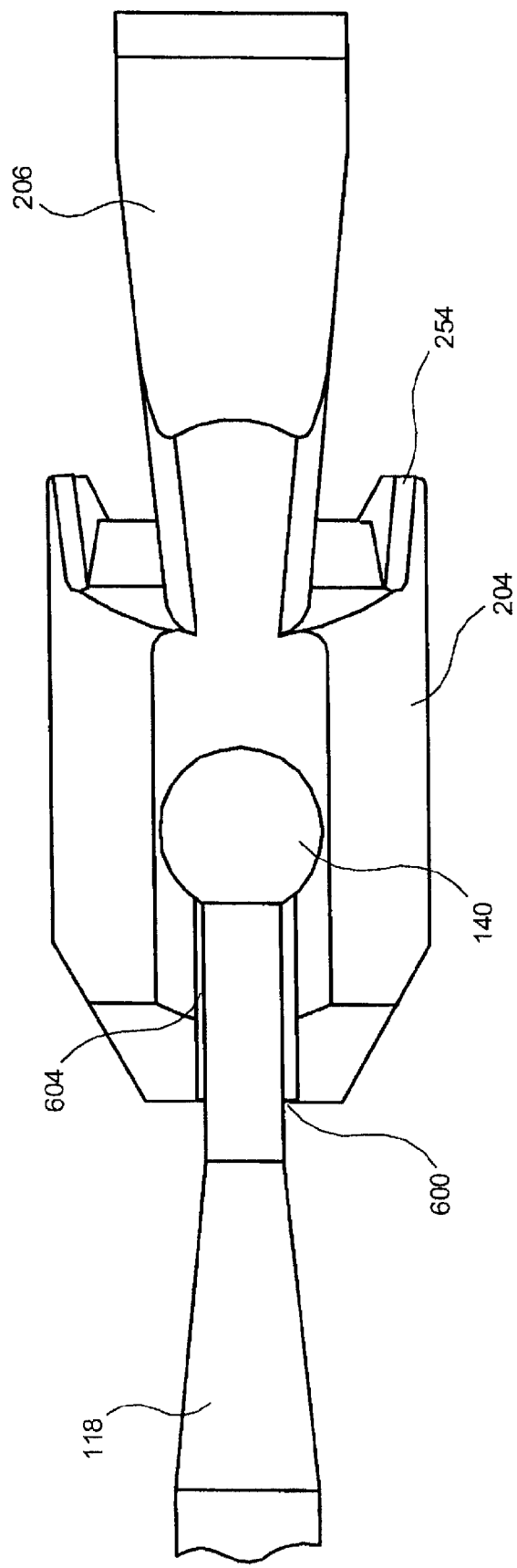
FIG. 29 is a top view of a yoke with a control wire according to an embodiment of the present invention.

Additional details of the yoke 204 are shown in FIGS. 27-29. When the control wire 118 is seated in the yoke 204, it is desirable to ensure that it cannot inadvertently be removed from the control wire slot 600. Accordingly, in the present embodiment the ball cavity 602 has a diameter sufficiently large to allow the ball 140 to pass therethrough while the wire cavity 604 is large enough to allow the control wire 118 to pass therethrough, but not large enough to allow the ball 140 pass therethrough. To assemble the control wire 118 with the yoke 204 according to the exemplary embodiment, the proximal end of wire 140 is inserted into the ball cavity 602 until the ball bottoms out, and then the control wire 118 is rotated until it is seated in the control wire cavity 604, thus constraining further movement of the ball 140. According to the present embodiment, the yoke 204 may be made of a biocompatible metal such as stainless steel or a high strength polymer such as Ultem™.

According to embodiments of the present invention, the clipping device 100 may be scaled to fit the requirements of different surgical procedures. In one exemplary embodiment, the clipping device 100 may be sized to fit through an endoscope having a working channel diameter of approximately 0.110 inches. The exemplary bushing may have a length of about 0.22 inches and an OD of approximately 0.085 inches. The capsule may have a length of about 0.5 inches, an OD of about 0.085 inches, and a wall thickness of about 0.003 inches. When assembled, the rigid length of the capsule 200 and the bushing 202 is approximately 0.625 inches. This length is important because if it is too great, the assembly will not pass through the bends of the flexible endoscope. In the exemplary clipping device, the outer sheath may have an ID of approximately 0.088 inches and an OD of about 0.102 inches. The overall length of the clipping device may be approximately 160 inches, while the tissue grasping portion of the clip arms 208 may be approximately 0.4 inches long.

In treating internal bleeding, and in particular to apply an hemostatic treatment to gastrointestinal bleeding, it is often necessary to apply more than one hemostatic clip to the injured tissue. Using conventional methods, the treatment involves repeatedly utilizing a single deployment clip apparatus, with the disadvantage of having to remove the old clipping device from the endoscope, prepare additional clipping devices, and re-inserting the additional clipping devices in the endoscope for each clip. After insertion in the endoscope, each additional device has to be re-positioned over the wounded tissue before the new clip may be deployed. Multi deployment clipping devices are also in use, but generally require the device to be removed from the endoscope so that a new clip may be loaded manually in the device.

In a further embodiment of the present invention, a multi-clip endoscopic hemostatic device may be used to discharge multiple hemostatic clips without the necessity to remove the device from the endoscope after each clip is deployed. The multiclip device achieves equal or better results than conventional single deployment clipping devices, while greatly facilitating the placement of multiple hemostatic clips in cases where a single hemostatic clip is insufficient. In one embodiment, the clips used by the multiclip device according to the present invention are substantially similar in size to conventional hemostatic clips, and thus can be used with conventional endoscopes. According to the invention, the cost of manufacturing the multiclip apparatus is sufficiently low to permit the units to be disposable, and be discarded after use with only one patient.

According to the invention, the multiclip hemostatic clipping apparatus is used in a minimally invasive environment, such that it is applied to the surgical site through an endoscope. The distal end of the hemostatic multiclip device is inserted through the working lumen of the endoscope, and is brought in the vicinity of the surgical site where the bleeding occurs. For example, an endoscope having a working channel of at least about 1.8 mm inner diameter may be used to reach the surgical site. The proximal ends of the endoscope and of the hemostatic multiclip device are provided with hand controls used by the user/physician to operate the devices.

The hemostatic multiclip device according to an exemplary embodiment of the present invention uses a magazine containing a plurality of hemostatic clips that is advanced through the endoscope's working lumen, to a location near the surgical site. The magazine may be attached to a sheath designed to protect the inner surfaces of the endoscope from damage caused by sharp edges of the magazine and clip assembly, and which extends beyond the magazine through the length of the endoscope. The hemostatic clips are joined in a clip chain which is inserted in the magazine, and is free to translate in the magazine within certain limits that will be described below. Each of the clips may be formed, for example, of sheet metal or of another material having appropriate mechanical and bio-compatibility properties. The material of the clips is selected to resist plastic deformation while constrained in the closed configuration, so that the hemostatic clips will return to the open configuration when not otherwise restrained.

A modified version of the clipping device 100, shown in FIGS. 1 and 2, may be used with the clip magazine and clip chain described above. A clip magazine containing multiple hemostatic clips may be inserted in the proximal end of the shaft section 104, such that the clips are deployed from the distal end thereof. A handle 108 and sliding spool 110, or similar implements, may be used in conjunction with a control linkage to operate the multiclip dispensing apparatus, as will be described in detail below.

Figure 31:
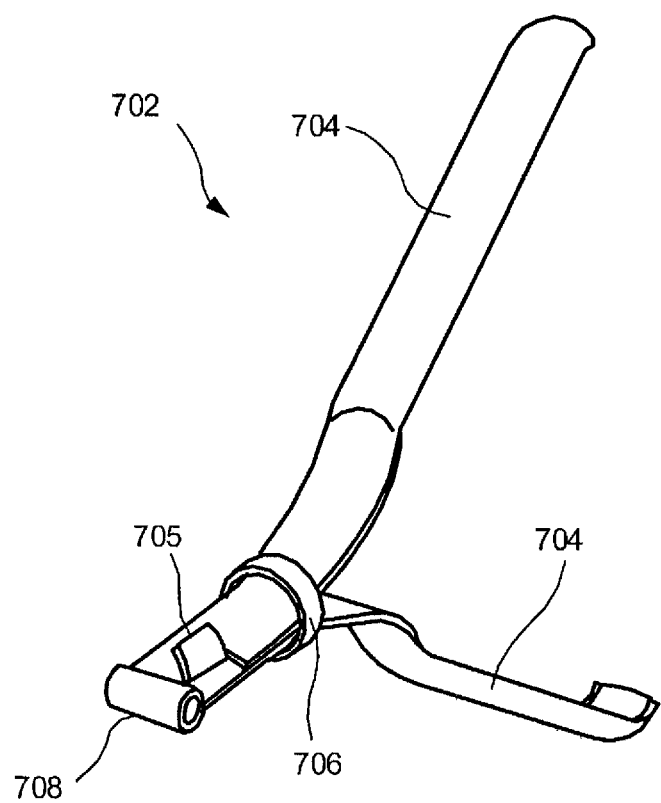
FIG. 31 shows a perspective view of an individual hemostatic clip of a clip chain according to an embodiment of the invention.

FIG. 31 shows an exemplary embodiment of a hemostatic clip according to the present invention. Exemplary clip 702 comprises two clip arms 704 which have inner facing surfaces adapted to grasp and retain tissue therebetween when placed in a closed configuration. In FIG. 31, the clip arms 704 are in the open configuration which is assumed by the clip 702 in the early phase of deployment, before the tissue is clamped. Clip 702 may be formed of two parts joined at the common portion 705, or may be of a single piece construction. In the exemplary embodiment, clip 702 is biased in the open configuration (shown in FIG. 31) prior to being loaded in the clip magazine. A sliding lock ring 706 may be used to lock clip arms 704 in the closed configuration, which is assumed by the clip 702 when it is clamped to the tissue. In different exemplary embodiments, the sliding locking ring 706 may be replaced by different devices adapted to lock clip arms 704 in the closed configuration.

As indicated above, a plurality of clips may be loaded in the magazine for use with the hemostatic multiclip device according to the present invention. FIG. 32 shows an exemplary embodiment of a clip chain according to the invention. Clip chain 700 is formed by joining hemostatic clips 702 to one another using, for example, a linking feature 708. Linking feature 708 may comprise an attachment which retains the two joined clips 702 together as long as there is no movement of the joined clip ends in a direction perpendicular to the longitudinal axis of the clips. In this manner, the clip chain 700 remains intact as long as the clips are translated in a direction generally along the longitudinal axis of the clips. One clip may be released, however, by moving the appropriate clip end along a diameter of the device, that is in a direction perpendicular to the longitudinal axis. For example, linking feature 708 may be clamped between the distal ends of clip arms 704 which are held in the closed configuration. Linking feature 708 may be formed integrally with the body of hemostatic clip 702, or may be an optional addition that may be attached to more conventional clips.

Figure 35:
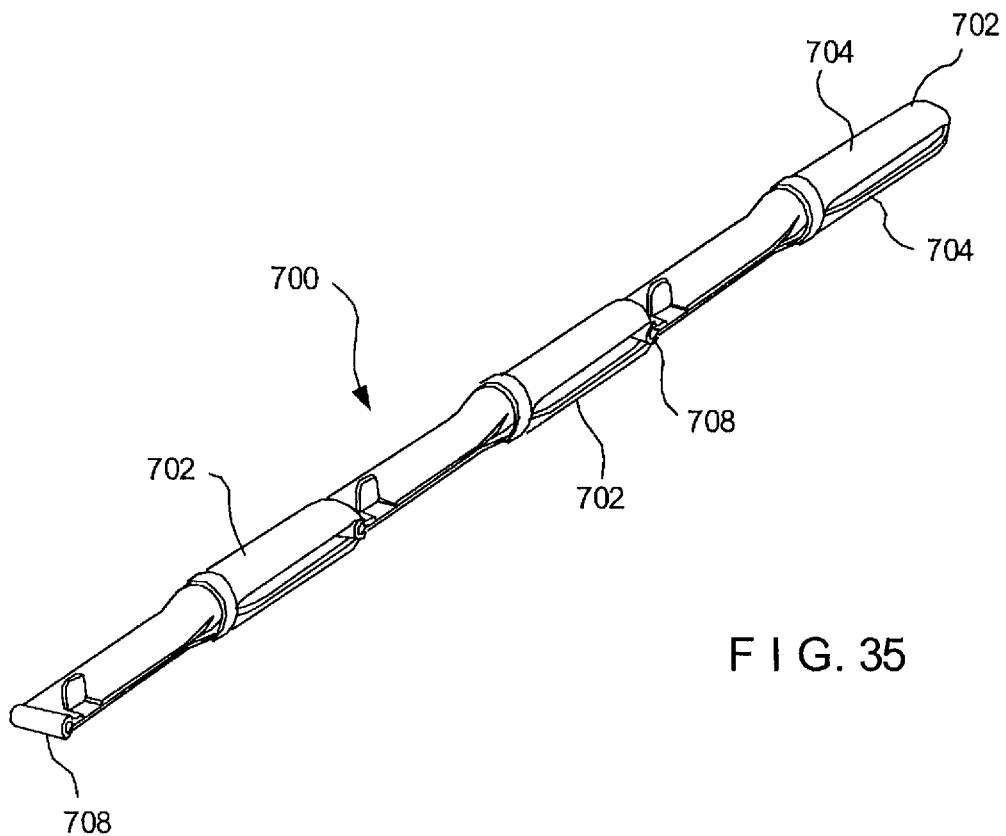
FIG. 35 shows a perspective view of the clip chain shown in FIG. 32.
Figure 36:
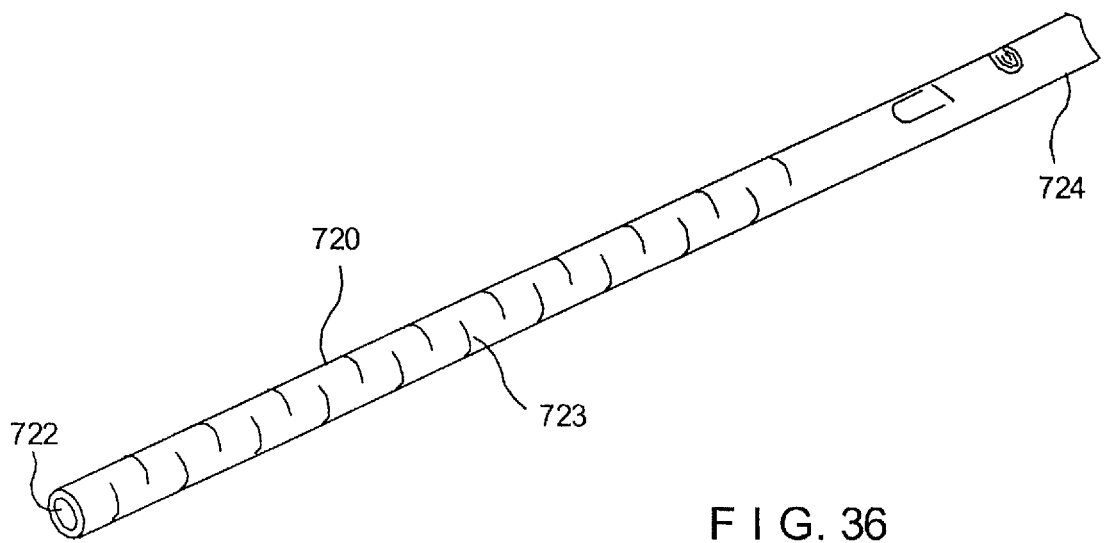
FIG. 36 shows a perspective view of a clip magazine according to an embodiment of the invention.
Figure 38:
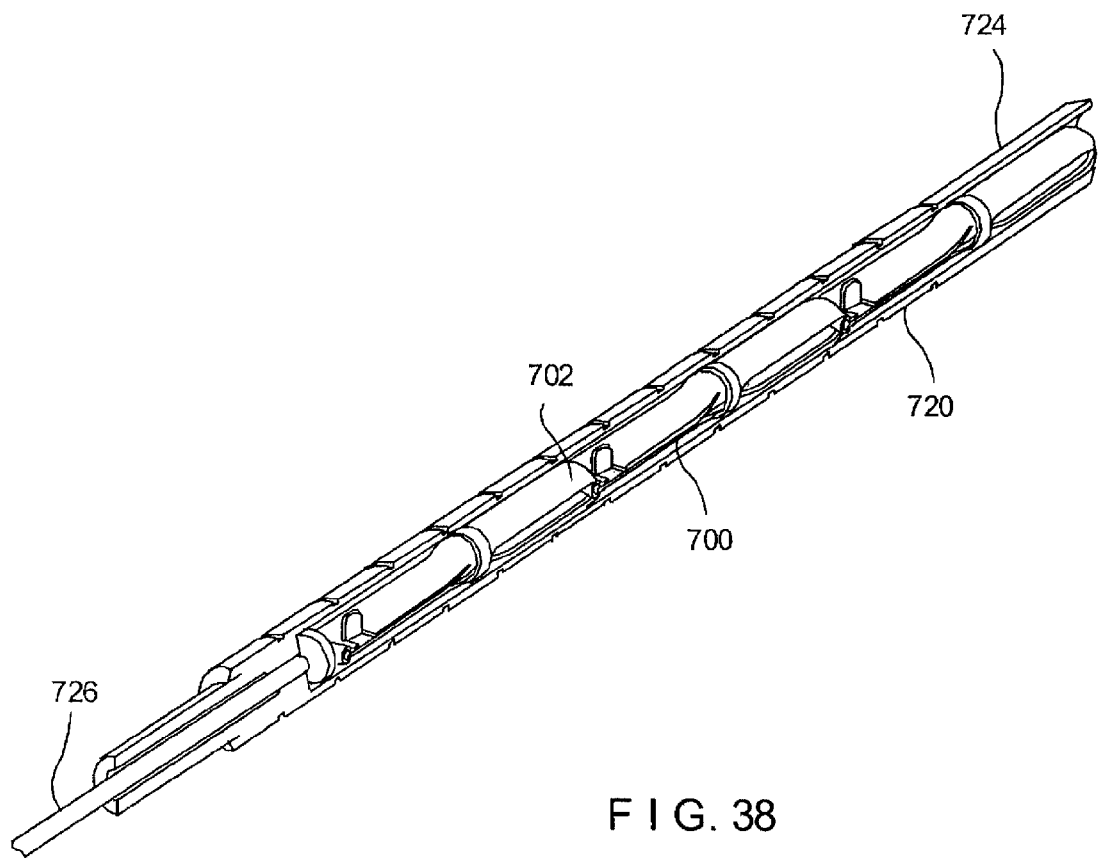
FIG. 38 shows a cut away perspective view of a clip chain loaded in a clip magazine according to an embodiment of the invention.

An exemplary clip magazine 720 is shown in perspective view in FIG. 36. Clip chain 700 (shown in perspective view in FIG. 35) may be inserted longitudinally in the hollow channel 722 of magazine 720, as shown in FIG. 38. Magazine 720 may be a generally cylindrical structure located at the distal end of the hemostatic multiclip device, which contains a portion or all of the clips 702 within the clip chain 700. Magazine 720, together with clip chain 700, forms a capsule having dimensions and sufficient flexibility to comply with the curvature of the endoscope's working channel. Compliance features 723 may be used to impart flexibility to the body of magazine 720, and for example may comprise circumferential slits. A control link 726 may enter a proximal opening 722 of the clip magazine 720, opposite from the distal end 724.

The most proximal of the clips 702 may be connected to control link 726 in a releasable manner. Control link 726 may be designed to carry compression and tension loads, so that clip chain 700 may be translated in both directions through forces transmitted by control link 726. Control link 726 may be formed by a rigid tube, a semi rigid wire, or by any other structural element capable of transmitting tension and compression loads along the length of the hemostatic multiclip device. Control link 726 may be connected to a control handle at the proximal end, to give to the surgeon control of the clip's deployment.

Figure 30:
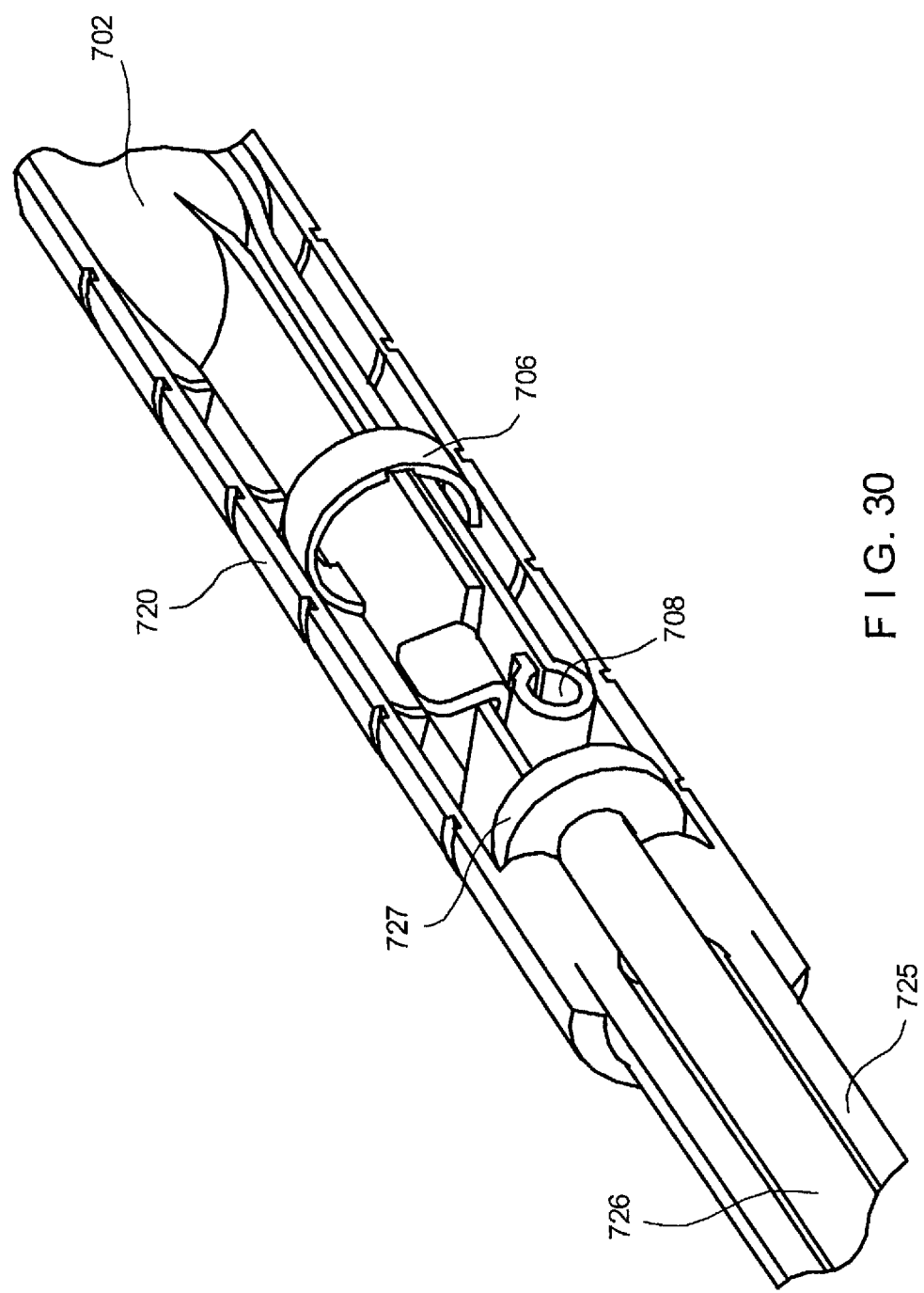
FIG. 30 shows a detail of a connection between a control link and a clip chain according to an embodiment of the invention.

FIG. 30 shows a detail of the connection between the control link 726 and the most proximal hemostatic clip 702. In this embodiment, control link 726 is a rod or tube which terminates in a connector portion 727 adapted to push against linking element 708. Connector portion 727 may also be designed to apply a tension force to the linking element 708, in a known manner. A sheath 725 may be used to encapsulate control link 726, to protect the working channel of an endoscope from damage, and to reduce friction between the moving control link 726 and the clip magazine 720.

A control handle portion of the hemostatic multiclip device (not shown) is provided at the proximal end of the device, extending outside of the proximal end of the endoscope. The control portion may be similar to that shown in FIG. 1, and may comprise hand controls which operate the control link 726 to cause the deployment and the release of the successive clips 702. For example, hand movements of the surgeon may be transformed within the control portion into longitudinal movements of the control link 726 along the working channel of the endoscope. In an exemplary embodiment, clip chain 700 is rigid in compression and supports tensile loads, at least while contained within the clip magazine 720. Clip chain 700 can therefore be translated along magazine 720 via movement of the control link 726.

As shown in FIG. 38, the clip chain 700 is formed of hemostatic clips 702 which remain attached to one another while they are within the cylindrical containment of the clip magazine 720. Clip magazine 720 supports and constrains the clips 702 of the clip chain 700 in the radial direction through a large portion of its length. This prevents pairs of adjacent clips 702 from disconnecting, by not allowing relative radial movement between two clips. In particular, the radial movement of the substantially closed clip arms 704 of a first hemostatic clip is prevented, so that the linking feature 708 of a second clip, adjacent to the first clip, is not released. The exemplary design of clip chain 700 helps to minimize the width of the device, since it is only as wide as the width of the clips themselves.

Figure 37:
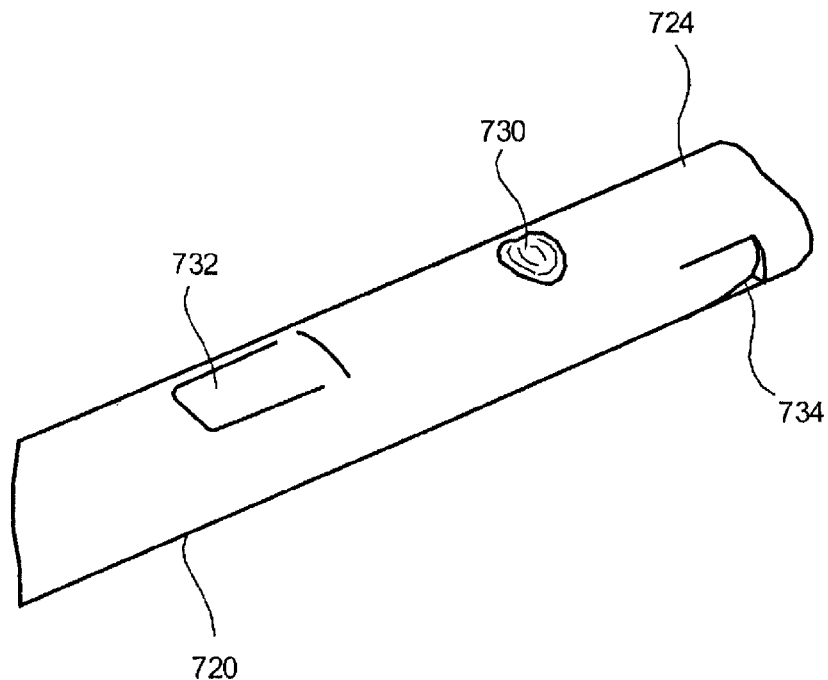
FIG. 37 shows a distal end detail of the clip magazine shown in FIG. 36.

The diameter of clip chain 700 works in conjunction with the shape of the distal end 724 of clip magazine 720 to control the position of the distal portion of clip chain 700 through the distal end 724. As shown in FIG. 37, magazine 720 has a reduced cross section portion 730 designed to limit the diameter of what passes therethrough. Specifically, reduced cross section 730 allows the passage of a single clip unattached to another clip at its distal end. However, reduced cross section 730 does not allow passage of a pair of connected clips. This is because the diameter of two connected clips is greater than the diameter of a single clip. In the exemplary embodiment that is due to the clip arms 704 not closing fully when they lock unto the linking feature 708 of another clip 702, resulting in a greater distal tip diameter of the clip.

The function of the clip chain 700 is better shown in FIGS. 39, 40, where a clip 702' is placed to lead the clip chain 700 through the distal end 724 and through cross section reduction 730. As the control element 726 is pushed distally, clip chain 700 is pushed distally until its second most distal clip 702 is stopped by reduced cross section 730, at a position where the most distal clip 702' is outside of magazine 720, and is biased in the open configuration ready to grasp the tissue. In FIG. 39, the most distal hemostatic clip 702' is being pushed outside of clip magazine 720, past the distal end 724. As the control link 726 continues to push distally, clip arms 704 of the second most distal clip 702 of chain 700 abut the reduced cross section 730 (FIG. 40). At this point the single distal clip 702' is largely outside of magazine 720, and its clip arms 704' take the open configuration since they are no longer constrained by magazine 720.

Once the user has placed the open clip 702' over the desired location on the tissue, control link 726 is pulled proximally, so that clip chain 700 (including the most distal clip 702') is pulled back into magazine 720, as shown in FIG. 41. Clip sliding lock ring 706 is held distally by lock ring anti-pull back tabs 734, as distal clip 702' is pulled proximally. This causes lock ring 706 to move partially over clip arms 704' and lock them in the closed configuration, to firmly grasp the tissue held within clips arms 704'. At this point the most distal hemostatic clip 702' is clamped securely over the tissue, but is still attached via linking feature 708 to the clip chain 700.

After deployment and clamping of the most distal hemostatic clip 702' is achieved, further proximal movement of the control linkage 726 causes separation of clip 702' from clip chain 700. Additional features may be formed on the clip 702' or on the lock ring 706 to cooperate with distal end 724 and prevent further proximal movement of the distal clip 702' relative to magazine 720. The pull back distance of distal clip 702' may be controlled, for example by properly positioning the additional feature 733, so that the link between the most distal clip 702' and the next to most distal clip 702 is located in a relief portion 732 of the distal end 724. Relief portion 732 may be a movable tab or opening which allows local diametrical expansion of the clips within that portion of magazine 720.

As continued proximal tension force is applied by control link 726, clip arms 704 of the second most distal clip 702 are pushed diametrically outward over the interlock feature 708 of the most distal hemostatic clip 702', which now acts as a cam surface. Relief portion 732 of the clip magazine 720 allows the outward expansion due to the outward movement of clip arms 704 over linking feature 708, thereby permitting clip arms 704 to continue moving proximally and separate from distal-most clip 702'. In other words, the separation of the two adjacent clips is caused by the force in the diametrical direction resulting from clip arms 704 being forced over clip lock feature 708 of distal clip 702', and this force overcoming the bias of relief portion 732. Distal most clip 702' is still prevented to further move proximally by the additional feature 733 described above, but is now free to move distally and exit magazine 720.

FIG. 42 depicts the situation where the "former" most distal hemostatic clip 702' has been ejected from clip magazine 720, and is clamped securely to the target tissue. A "new" most distal hemostatic clip 702 has been pushed partially out of magazine 720, and its clip arms 704 are in the open configuration, outside of distal portion 724. The new most distal clip 702 is still connected to another clip 702 which is fully inside of clip magazine 720, and is part of clip chain 700. The user may at this point position open clip arms 704 over the desired tissue, and repeat the process described above to clamp clip arms 704 over the tissue, lock them closed, and release the new distal-most clip 702 from the clip chain 700 and from clip magazine 720.

To release the most distal clip 702' from the clip chain 700, the clip arms 704 belonging to the clip 702, adjacent to the clip 702', have to disengage from the linking feature 708'. To do so, the distal tip of clip arms 704 has to open at least sufficiently to clear the linking feature 708' of the most distal clip 702'. The clip 702 is contained within the magazine 720, which because of its radially rigid construction, for the most part prevents the clip arms 704 from opening. The only time that the clip arms 704 can open and release the linking feature 708' is when the distal tips 705 of the clip arms 704 are substantially aligned with a section of the magazine 720 which either is radially wider, or is designed to yield when pressed by the clip arms 704. For example, the relief portion 732 may comprise a cut out opening or a non-rigid portion of the magazine's wall, dimensioned to accommodate the tips 705 of the clip arms 704.

The utility of the multi clip deployment device according to the invention may be increased by configuring the multi-clip magazine so that the release of the linking feature 708' from clip arms 704 can be performed more easily. In an additional exemplary embodiment shown in FIG. 43, the magazine 800 is formed with an expanded section 804 which extends 360 degrees around the circumference of the magazine 800. The expanded section 804 formed by the wall of the magazine 800 defines an expanded chamber 810 within the lumen of magazine 800. The expanded chamber 810 provides for sufficient room within the magazine 800 to allow distal tips 705 of the clip arms 704 to move radially outwards, as the clip arms 704 open to pass over the linking feature 708'.

The deployment of the most distal clip 702' from the exemplary magazine 800 is in many respects similar to the deployment from the magazine 720, described above. A control link 726 may be used to transfer commands from the surgeon to the clip deployment mechanism in the form of proximal and distal translation of the link 726. The most distal clip 702' is initially connected to a clip chain 700, and may be translated forward and backwards while still connected to the adjacent clip 702. After the surgeon places the distal end of clip 702' in position over the target tissue 822, the most distal clip 702' is pulled back inside the magazine 800, so that clip arms 704' close over a portion 820 of the target tissue 822. The lock ring 706' may be pushed distally by distal lip 806 of the magazine 800, to lock the clip arms 704' in the closed position around the target tissue portion 820.

After the most distal clip 702' is clamped and locked in the closed position around the portion of target tissue 820, further proximal movement of the clip 702 causes the distal clip 702' and its adjacent clip 702 to detach. For the purposes of this discussion, clip 702 is referred to as the next-to-most distal clip. More specifically. The distal ends 705 of the adjacent clip's arms 704 partially open to pass over the linking feature 708' of the most distal clip 702', under the traction applied by the control linkage 726 which pulls clip 702 proximally. As described above, the most distal clip 702' is prevented from moving proximally by the shape of the distal end 806 of the magazine 800, so that a tension exists between the most distal clip 702' and the next-to-most distal clip 702. As the clip 702 moves proximally, linking feature 708' acts as a cam forcing the clip arms 704 to open. The expanded chamber 810 allows the radial opening of the clip arms 704, which releases the linking feature 708'.

The magazine 800 provides several benefits to the multi-clip deployment device according to the present invention. Since the expanded section 804 is a radial bulge which spans 360 degrees around the circumference of the magazine 800, the rotational orientation of the clip chain 700, which includes clips 702 and 702', within the magazine 800 is not important. The surgeon therefore has greater liberty to orient the distal clip 702' as necessary to best perform the procedure. The rotational orientation of the clip chain 700 may be changed relative to the orientation of the magazine 800 and of the entire multi-clip delivery device to which the magazine 800 is attached, to better align the clip with the target tissue. This configuration simplifies the clip deployment procedure and makes the entire procedure simpler and less time consuming. In addition, manufacturing of the magazine 800 can be simpler, since there is no need to process the magazine to form radial relief regions such as relief portions 732, or to cut openings in the wall of the magazine 800.

An exemplary clip deployment sequence from a magazine 800 according to the present invention is described below. FIGS. 44-48 are used to depict the deployment of a most distal clip 702' from the magazine 800. FIG. 44 depicts a pre-deployment configuration of the most distal clip 702' from the magazine 800, such that the clip arms 704' are completely within the distal portion 802 of the magazine 800. In this configuration, the linking feature 708' is being grasped by the clip arms 704 of the clip 702, such that the two clips 702, 702' are connected in the clip chain 700. The lock ring 706' is away from the clip arms 704', and does not yet constrain them in the closed configuration. In this step of the deployment, the surgeon may position the distal tip 802 of the magazine 800 in proximity of the target tissue, while preparing to clamp the clip 702' to that tissue.

As the control link 726 is pushed distally during a distal stroke of the deployment sequence, clip 702' is pushed outside of the magazine 800, as shown in FIG. 45. In this configuration, the arms 704' of clip 702' are no longer constrained by the walls of the magazine 800. The lock ring 706' is still near the clip's proximal end, held by the tip 802 within the magazine 800, so that the clip arms 704' are free to move to the open configuration. At this point, the clips 702, 702' are connected by means of the linking feature 708', and are free to rotate 360 degrees in any rotational orientation within the magazine 800 to facilitate proper orientation relative to the tissue to be clamped. Using the ability to place the clip 702' in any desired rotational orientation, the surgeon can orient the clip arms 704' in any desired position over the target tissue 820, so that closing the clip arms causes the tissue to be clamped as effectively as possible.

When the clip arms 704' are correctly placed in the proper orientation over the target tissue 820, the surgeon may continue the deployment by carrying out a proximal stroke of the deployment sequence. This causes the control link 726 to move proximally, thus entraining clip 704 and clip 704'. As described in the context of other embodiments, the proximal stroke of control link 726 causes the clip arms 704' to close, and clamp on the portion 820 of the target tissue 822. Distal end 802 of the magazine 800 forces the clip arms 704' to close as clip 702' moves proximally inside of the magazine 800, such that the target tissue is clamped, as shown in FIG. 46. The lock ring 706' is held near distal tip 802 by protrusions within magazine 800, and slides distally over the clip arms 704' as they are pulled proximally within the magazine 800. In this manner, the clip arms 704' are securely locked in the closed configuration by ring 706', and are clamped on the target tissue. After the clip arms 704' are locked in the closed configuration on the target tissue, the magazine 800 and the rest of the device can be rotated relative to the clips 702, 702', since these are free to turn 360 degrees within the magazine 800.

Figure 47:
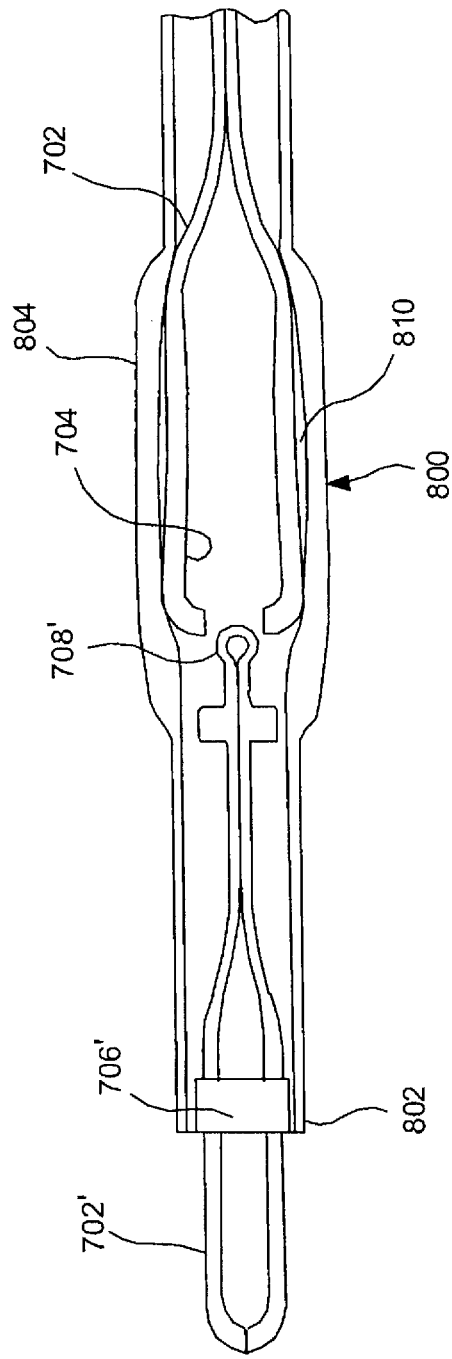
FIG. 47 is a cut-away diagram showing one of the clips of FIG. 44 being disconnected from the other clip.

Continued proximal tension on the control link 726 causes the clip 702 to further move proximally within the magazine 800. FIG. 47 depicts this step of the clip deployment process. However, the most distal clip 702' is prevented from further proximal movement by the lock ring 706' interacting with the protrusions formed at the distal end 802 of the magazine 800. Lock ring 706' is also prevented from moving too far distally over the closed clip arms 704' by ring stops 705. Accordingly, clip arms 704 are pushed apart by the linking feature 708, which acts as a cam as the tip of clip arms 704 pass over it. The expanded chamber 810 defined by the expanded section 804 of magazine 800 gives sufficient room to the clip legs 704 to open and pass over the linking element 708', so that the clip 702 can disengage from the clip 702'. Expanded section 804 extends 360 degrees around the circumference of the magazine 800, so that the orientation of clips 702, 702' within the magazine 800 is not important. This makes it possible for the surgeon to change the rotational orientation of the clip 702' relative to the magazine 800 throughout the deployment steps, to maintain the desired orientation between the clip 702' and the target tissue 822.

Figure 48:
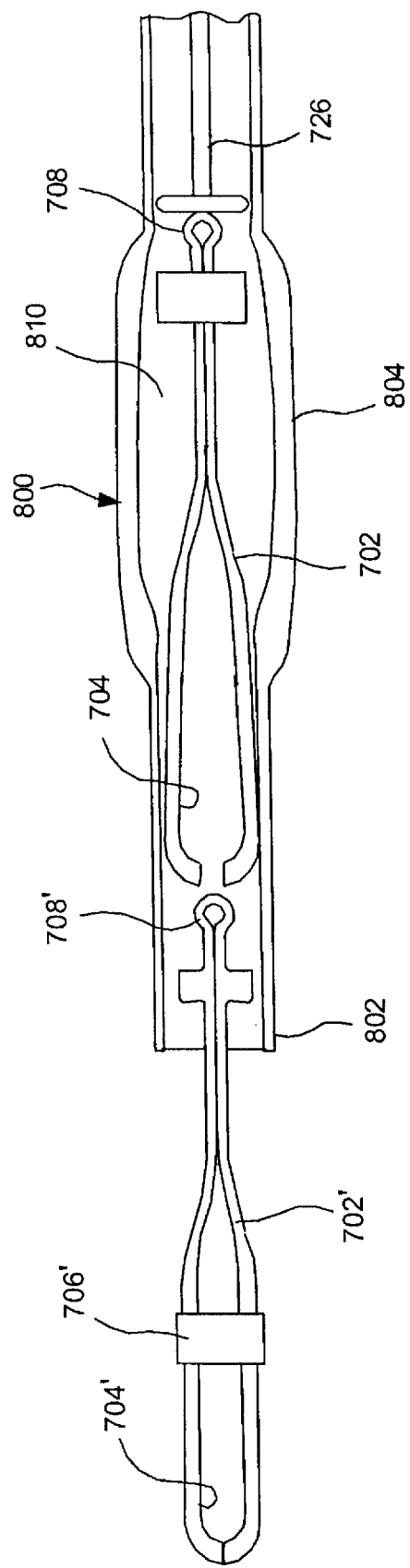
FIG. 48 is a cut-away diagram showing one of the clips of FIG. 44 deployed from the magazine.

FIG. 48 depicts the final step of the clip deployment sequence, in which the clip 702' is released from the magazine 800 and is left clamped to the target tissue. In this step, control link 726 may be again moved distally, to push clips 702 and 702', which are now disconnected. As shown, clip 702' is pushed outside of the magazine 800 by the distal portion of clip 702, until it is ejected from the magazine 800. Clip 702 now becomes the most distal clip present in the magazine 800, and the same steps described relative to carry out the deployment of clip 702' may be repeated to deploy the new clip 702. Although the drawings depict a magazine 800 containing only two clips 702 and 702', it will be apparent to those of skill in the art that additional clips may be connected in the same manner within magazine 800, to form a longer clip chain 700.

As described, the distal most clip 702' after release from the clip chain 700, or more simply from clip 702, may exit clip magazine 800 due to the tension applied to it by the clamped tissue. Alternatively, clip 702' may be pushed out by the distal movement of clip 702, as it is pushed towards the distal end 802. The surgeon may ensure a complete release of clip 702' by causing the control link 726 to move distally, for example by manipulating the hand control of the device. Conventional methods may be used to transform the hand movements of the surgeon into translation of the control link 726, and to carry out the initial distal stroke and the subsequent proximal stroke.

The present invention has been described with reference to specific exemplary embodiments. Those skilled in the art will understand that changes may be made in details, particularly in matters of shape, size, material and arrangement of parts without departing from the teaching of the invention. Accordingly, various modifications and changes may be made to the embodiments without departing from the broadest scope of the invention as set forth in the claims that follow. The specifications and drawings are, therefore, to be regarded in an illustrative rather than a restrictive sense.

What is claimed is:

1. A multi clip magazine for surgical procedures, comprising:
   a substantially cylindrical shell;
   a proximal end of the shell adapted for connection with a clip deployment apparatus;
   a central lumen for containing a clip chain rotatable therein; a distal end of the shell having a clip deployment opening and surface features adapted to facilitate opening and to cause closing and locking of a distal-most clip of the clip chain; and
   an expanded portion of the shell providing a region for the next clip immediately proximal to the distal-most clip to open and release the distal-most clip while the next clip is in any rotational orientation, wherein the expanded portion extends 360 degrees around a circumference of the shell, wherein the expanded portion comprises a circumferential bulge of the shell having a radius increased with respect to proximal and distal portions of the shell.

2. The multi clip magazine according to claim 1, wherein the proximal end is adapted to receive a control link operatively connectable to the clip chain.

3. The multi clip magazine according to claim 1, wherein the circumferential bulge has a radius substantially corresponding to a dimension of the next clip when opened sufficiently to release the distal-most clip.

4. The multi clip magazine according to claim 1, wherein the expanded portion is symmetrical with respect to a longitudinal axis of the multi clip magazine.

5. The multi clip magazine according to claim 1, wherein the clip chain comprises hemostatic clips.

6. The multi clip magazine according to claim 1, wherein the shell is adapted for insertion into a patient through an endoscopic instrument.

7. The multi clip magazine according to claim 1, further comprising distal surface features adapted to move a locking ring of the distal-most clip to a clip locking position.

8. The multi clip magazine according to claim 1, wherein the shell outside of the expanded portion has a diameter corresponding to a dimension of closed clips of the clip chain.

9. The multi-clip magazine of claim according to claim 1, wherein the circumferential bulge defines an increased diameter of central lumen.

10. A multi clip magazine for surgical procedures, comprising:
    a substantially cylindrical shell;
    a proximal end of the shell adapted for connection with a clip deployment apparatus;
    a central lumen for containing a clip chain rotatable therein; and
    an expanded portion of the shell providing a region for the next clip immediately proximal to the distal-most clip to open and release the distal-most clip while the next clip is in any rotational orientation, wherein the expanded portion comprises a circumferential bulge of the shell having a radius increased with respect to proximal and distal portions of the shell and wherein:
    a distal end of the shell includes a clip-deployment opening bounded by a distal lip against which a locking element may be pushed into a locking configuration over arms of the distal-most clip.

11. The multi clip magazine of claim 10, wherein the circumferential bulge has a radius substantially corresponding to a dimension of the next clip when opened sufficiently to release the distal-most clip.

12. The multi clip magazine according to claim 10, wherein the expanded portion is symmetrical with respect to a longitudinal axis of the multi clip magazine.

13. The multi-clip magazine of claim 10, wherein the circumferential bulge defines an increased diameter of central lumen.

* * * * *